(12) United States Patent
Kaufman et al.

(10) Patent No.: US 11,219,575 B2
(45) Date of Patent: Jan. 11, 2022

(54) REAL-TIME KINEMATIC ANALYSIS DURING CARDIO-PULMONARY RESUSCITATION

(71) Applicant: ZOLL Medical Corporation, Chelmsford, MA (US)

(72) Inventors: Christopher Luke Kaufman, Somerville, MA (US); Ulrich Herken, Medford, MA (US); Gary A. Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 363 days.

(21) Appl. No.: 15/463,678

(22) Filed: Mar. 20, 2017

(65) Prior Publication Data
US 2017/0273864 A1   Sep. 28, 2017

Related U.S. Application Data

(60) Provisional application No. 62/311,987, filed on Mar. 23, 2016.

(51) Int. Cl.
*A61H 31/00* (2006.01)
*A61N 1/39* (2006.01)
(Continued)

(52) U.S. Cl.
CPC ......... *A61H 31/005* (2013.01); *A61N 1/3937* (2013.01); *A61N 1/3993* (2013.01);
(Continued)

(58) Field of Classification Search
CPC ...... G09B 5/065; G09B 23/288; G09B 23/28;
G09B 23/30; G09B 19/03; G09B 5/06;
G09B 19/003; A61H 31/005; A61H
31/007; A61H 2201/5007; A61H
2201/5012; A61H 2201/5043; A61H
2201/5058; A61H 2201/5064; A61H
2201/5084; A61H 2230/06; A61H
2230/08; A61H 2230/085; A61H
2230/207; A61H 2230/50; A61H
2201/5094; A61H 2230/062; A41D
2400/32; A41D 2400/322; A61N 1/3937;
A61N 1/3993
(Continued)

(56) References Cited

U.S. PATENT DOCUMENTS 6,201,992 B1 * 3/2001 Freeman ................... A61N 1/39
607/5
6,961,612 B2   11/2005 Elghazzawi et al.
(Continued)

OTHER PUBLICATIONS

Haptic Clothing: The Futhre, May 1, 2014, Cover (Year: 2014).*

*Primary Examiner* — Jerry-Daryl Fletcher
(74) *Attorney, Agent, or Firm* — Fish & Richardson P.C.

(57) ABSTRACT

Systems and methods related to the field of cardiac resuscitation, and in particular to devices for assisting rescuers in performing cardio-pulmonary resuscitation (CPR) are described herein. The system includes a camera to capture one or more images at a scene where the person in need of medical assistance is being treated and one or more processors. The processors receive and process the images, by using a rescuer profile, to provide a real-time feedback to the rescuer to improve the CPR treatment.

30 Claims, 22 Drawing Sheets

(51) Int. Cl.
  *G09B 5/06*  (2006.01)
  *G09B 23/28*  (2006.01)
  *G09B 19/00*  (2006.01)

(52) U.S. Cl.
  CPC ........... *G09B 5/065* (2013.01); *G09B 23/288* (2013.01); *A41D 2400/32* (2013.01); *A41D 2400/322* (2013.01); *A61H 31/007* (2013.01); *A61H 2201/5007* (2013.01); *A61H 2201/5012* (2013.01); *A61H 2201/5043* (2013.01); *A61H 2201/5058* (2013.01); *A61H 2201/5064* (2013.01); *A61H 2201/5084* (2013.01); *A61H 2201/5094* (2013.01); *A61H 2230/06* (2013.01); *A61H 2230/08* (2013.01); *A61H 2230/085* (2013.01); *A61H 2230/207* (2013.01); *A61H 2230/50* (2013.01); *A61H 2230/62* (2013.01); *G09B 19/003* (2013.01)

(58) Field of Classification Search
  USPC ......................................... 434/265, 262, 267
  See application file for complete search history.

(56) References Cited

U.S. PATENT DOCUMENTS

| | | | | |
|---|---|---|---|---|
| 2005/0251213 | A1* | 11/2005 | Freeman | G09B 23/288 607/5 |
| 2008/0221487 | A1* | 9/2008 | Zohar | A61B 5/224 600/595 |
| 2010/0014717 | A1* | 1/2010 | Rosenkrantz | G06K 9/00885 382/115 |
| 2011/0117529 | A1* | 5/2011 | Barash | G09B 23/288 434/265 |
| 2012/0183940 | A1* | 7/2012 | Aragones | A63B 22/001 434/247 |
| 2013/0282069 | A1* | 10/2013 | Thiagarajan | A61N 1/3993 607/3 |
| 2013/0296719 | A1* | 11/2013 | Packer | A61B 5/0205 600/484 |
| 2013/0330697 | A1* | 12/2013 | Totman | G09B 23/288 434/265 |
| 2014/0342330 | A1* | 11/2014 | Freeman | G09B 23/288 434/265 |
| 2014/0342331 | A1* | 11/2014 | Freeman | A61H 31/005 434/265 |
| 2015/0105129 | A1* | 4/2015 | Chapman | A63F 13/285 463/7 |
| 2015/0255005 | A1* | 9/2015 | Yoda | G06T 17/00 434/265 |
| 2015/0325148 | A1* | 11/2015 | Kim | G09B 5/02 434/265 |
| 2016/0030758 | A1* | 2/2016 | Guiney | A61N 1/3925 607/5 |
| 2016/0030834 | A1* | 2/2016 | Brown | A63F 13/21 463/36 |
| 2017/0154230 | A1* | 6/2017 | Dow | G06K 9/00879 |
| 2018/0040255 | A1* | 2/2018 | Freeman | A61H 31/00 |
| 2018/0147113 | A1* | 5/2018 | Dellimore | A61H 31/005 |
| 2020/0167513 | A1* | 5/2020 | Holz | G06K 9/00355 |

* cited by examiner

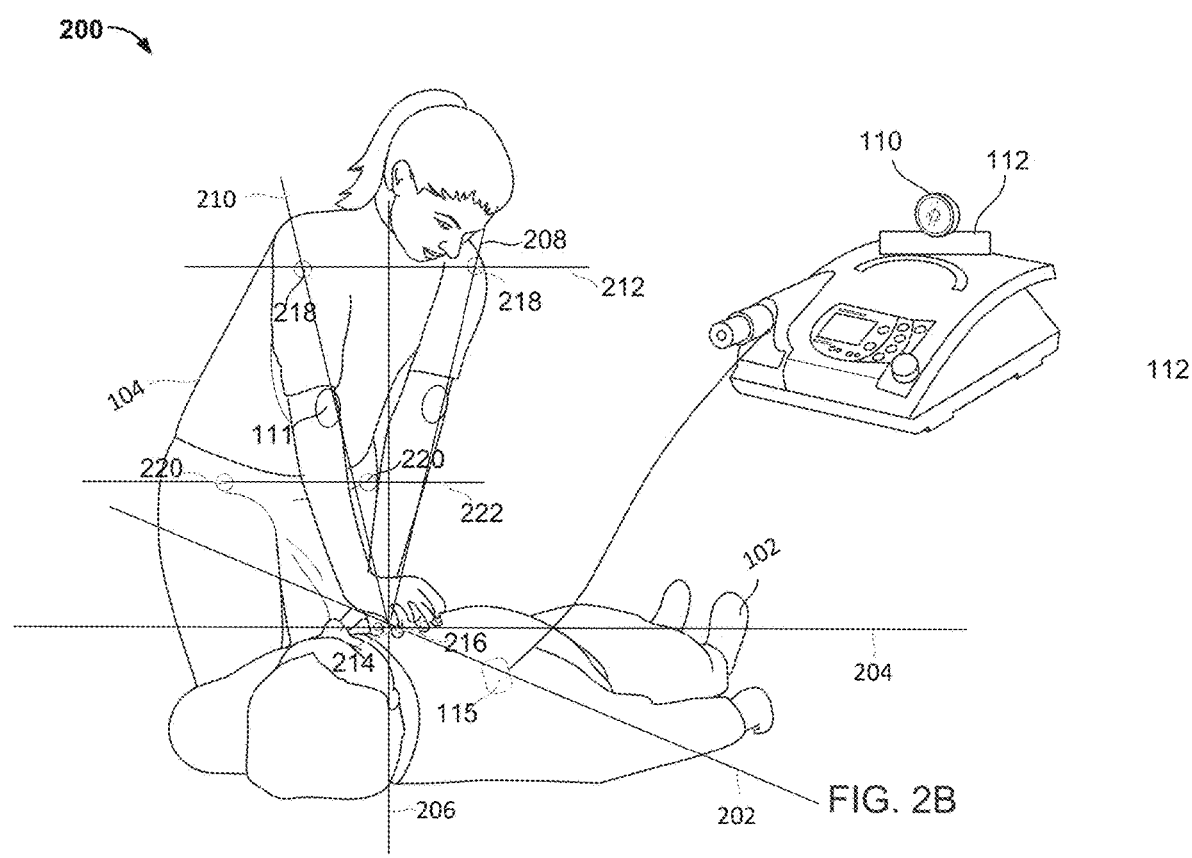

REAL-TIME KINEMATIC ANALYSIS DURING CARDIO-PULMONARY RESUSCITATION

CLAIM OF PRIORITY

This application claims priority under 35 USC § 119(e) to U.S. Patent Application Ser. No. 62/311,987, filed on Mar. 23, 2016, the entire contents of which are hereby incorporated by reference.

TECHNICAL FIELD

This document relates to cardiac resuscitation systems and techniques, and in particular to systems and techniques for assisting rescuers in performing and optimizing cardiopulmonary resuscitation (CPR).

BACKGROUND

CPR is a process by which one or more rescuers can provide chest compressions and ventilation to a patient who has suffered a cardiac arrest. Chest compressions are considered to be the most important element of CPR during the first five to eight minutes after CPR efforts begin, because chest compressions help maintain circulation through the body, heart, and brain, which are the organs that can sustain the most damage from an adverse cardiac event. Many factors, such as the depth of chest compression, the location of the applied pressure, and the timing of the chest compressions, can affect the outcome of CPR. Generally, American Heart Association CPR Guidelines define protocols by which a rescuer is to apply the chest compressions in coordination with ventilations. For example, current 2015 AHA Guidelines specify a ratio of 30:2 for compressions to ventilations (e.g., thirty compressions for every two breaths) and compressions are to be performed at a rate of between 100 and 120 per minute. Assisting an unexperienced rescuer with optimizing the factors that affect CPR outcome, according to appropriate CPR protocol, can increase the success of the treatment.

SUMMARY

This document describes systems and techniques that can be used to help manage the work by teams of rescuers who are responding to a patient, or person in need of emergency assistance. For example, typically such teams include a pair of rescuers, where a first of the rescuers performs CPR chest compressions on the patient and the other performs ventilations, either by mouth-to-mouth techniques or using a flexible ventilator bag. Frequently such teams are made up of an EMT or ambulance crew. Also frequently, a good heartbeat cannot be established quickly for the patient, so that CPR must be carried out for many minutes in order to maintain perfusion of blood in the patient. In such situations, rescuers can tire after only a minute or two of providing chest compressions, so that some protocols call for the rescuers to switch roles periodically. The systems and techniques provided by the current disclosure arise from a recognition that different people have different levels of skill, strength, and stamina for performing chest compressions, as well as other components of CPR such as ventilating a patient or administering drugs to the patient. For example, techniques described herein involve monitoring the quality of some components of CPR as it is being performed, such as by monitoring the depth and rate of chest compressions being performed, and informing rescuers to adjust their technique and/or to switch out when a component indicates that the performance of the chest compressions or other CPR component is inadequate, and might be, or would be, performed better by the other rescuer who is presumably more "fresh" or less fatigued.

Additionally, there can be parameters of body positioning and subtleties of motion different body segments (e.g. arms, torso, hips, head, shoulders, etc.) of the rescuer during chest compressions that may lead to better blood flow to the patient if these parameters are adjusted by the rescuer to deliver more optimal blood flow. These can be subtle parameters that are not easily notice by a particular rescuer, in much the same way that highly trained athletes review videos after a game to optimize golf or baseball swings to hit the ball farther and straighter. These parameters of positioning or motion may include: position of the shoulders relative to the position of the hands, angle of the arms at the elbow, the change of the angle of the arms at the elbow as the chest is compressed and released, the spacing of the shoulders relative to the patient as the chest is compression or released, the position of the rescuer's head relative to the patient, the position of the rescuer waist relative to the rescuer waist and the patient sternum.

Alternatively, or in addition, cameras can be provided at any suitable location, such as on a patient, on rescuers, on vehicles driven by the rescuers and/or on equipment used by the rescuers. For example, each rescuer can be provided with glasses or other wearable components that include forward-facing cameras for capturing generally what is in the field of view of each respective rescuer as they work. Similarly, the rescuers can mount a camera to the patient, such as by adhering a patch with an attached camera to the patient's forehead or another relatively stationary location that has a broad field of view. Cameras on vehicles and/or equipment can obtain a higher and broader view of a scene, such as by viewing downward toward the rescuers. Such cameras can capture 360 degree panaromas (e.g., via cameras similar to those used with Google StreetView® implementations, where images from adjacent cameras can be stitched together to form a 360 degree image so that the camera is in effect a 360 degree camera) and/or can be aimed toward the rescuers using signals from beacons worn by the rescuers or their medical equipment (e.g., monitors and defibrillators). In some implementations, the cameras can include multiple 360 degree cameras and/or light-field cameras whose focus distance can be adjusted with software post-capture—in such a way, objects at different distances from the camera can be made to be the focus by people or software that is analyzing the images remote from the emergency, either at the time of the rescue or a later time.

The images captured by the cameras (which can be captured every few seconds, every second, or multiple times per second up to video speeds) can be used for a variety of purposes. For example, the camera(s) can be used to record images of a rescuer so that a processor may receive and analyze the images to determine the body position of the rescuer performing CPR. Based on the analyzed images, the system may then provide real-time feedback (e.g., audio, visual, haptic) to the rescuer to improve the manner in which CPR is provided, which may affect the outcome of CPR treatment. In some cases, the rescuer(s) may wear one or more haptic feedback components, which can be used in connection with the analyzed images, to provide haptic feedback to the rescuer at pointed locations of the body, for improving the manner in which CPR is provided, and overall outcome of CPR treatment.

Or, the images can be used to identify the rate and depth of chest compression that are performed on a patient in the field of view of one or more of the cameras. Also, experts can use the images to conduct a code review to determine the effectiveness of the rescuers during a rescue. Also, the images can be used manually or automatically in combination with the techniques for switching rescuers in particular roles, in order to determine which rescuer is performing in each role at any particular period of time, and not merely that a change has occurred. To that end, near field communications chips can be worn by the rescuers (e.g., in wristbands) to further identify the locations of particular rescuers, such as when the NFC chip is near a reader or chip in a CPR puck on a patient's torso. The captured images can also be combined into a single larger image or panorama to provide a complete and immersive images of a rescue scene, such as for later review or for an offsite person to more fully experience the situation at the rescue site. The composite view can be provided to a remote location for review, such as by virtual reality techniques.

In some implementations, such systems and technique can provide one or more advantages. For example, a patient can be provided with the best care that is available from the rescue team throughout a rescue episode. For example, a rescuer with greater stamina can be left performing chest compressions longer than another rescuer with less stamina, whereas they might have been allowed to perform for equal time periods, with substandard performance, using techniques other than those described here. Also, the terms of each cycle can change as the rescue continues—e.g., by shortening the cycles as each of the rescuers gets more tired. Such adjustments can be dynamic and need not rely on a static timed schedule. Also, the system can identify erosion in performance even when the rescuers themselves do not recognize that their performance has eroded. Such identification can occur by measures external to the rescuer, such as their rate and depth of providing chest compressions, or measures internal to the rescuer, such as by measuring their blood oxygen level and pulse rate. The instructions to switch can also be provided in a clear and simple manner (and in a variety of manners, such as audibly or on a visual display next to the hands of the rescuer performing chest compressions), so that even rescuers in a high-stress environment can get the message (and the instructions can be provided at an increasing severity level if the system determines that the rescuers are not responding to the original instructions).

Moreover, in some implementations, such techniques can be used on teams of two, three, or more rescuers. In addition, in some implementations, the techniques can be implemented as part of an automatic external defibrillator (AED) or a professional defibrillator, or in a dual-mode defibrillator. As a result, the clinical performance of a rescuing team can be increased, and patient outcomes improved. Also, cameras can be used to capture images of a scene for later review of the performance of a rescue, or to be transmitted to a remote site in real time for review (e.g., by disaster management personnel for large-scale accidents, or by a physician who is monitoring a particular EMT rescue operation).

In one implementation, a system for managing a cardiopulmonary resuscitation (CPR) treatment to a patient in need of emergency assistance by a rescuer can be disclosed. The system can include: a camera configured to capture images of a rescuer performing the CPR treatment, and one or more processors, in communication with the camera. The processors can be configured to: receive the images of the rescuer, analyze the images to determine a body position of the rescuer, and cause a real-time feedback to be provided to the rescuer to improve a manner, in which CPR treatment can be provided based on the analyzed images. The one or more processors can be configured to compare the body position to data representing a template position, and based on the comparison, cause the real-time feedback. The template positon can be selected based on data representing physical characteristics of the rescuer, wherein at least one of the physical characteristics can be relevant to an ability of the rescuer to perform the CPR treatment.

In some aspects, the profile associated with the rescuer can include data representing physical characteristics of the rescuer, wherein the profile can be at least one of an expert profile, an intermediate profile, a novice profile, a default profile, and a profile that can be optimized for the given rescuer based off of previous testing/mock rescue attempts. The data representing physical characteristics of the rescuer can include data representing at least one of a body type, a time interval to fatigue and a history of training. The template position can be selected based on a profile associated with the rescuer. The body position of the rescuer can be a static body position. The body position of the rescuer can be a dynamic body position. The real-time feedback can be provided to the rescuer in a sequence of instructions based on a phase of the CPR treatment. The one or more processors can be configured to analyze the images to determine characteristics of a rescuer motion over one or more periods of time.

In other aspects, the one or more processors can be configured to analyze the images by generating a three dimensional representation of a rescue scene, the three dimensional representation can include a first representation of at least a portion of the rescuer and a second representation of at least a portion of the patient in need of emergency assistance by the rescuer. The three dimensional representation of the rescue scene can include removing information sufficient to identify the patient from the three dimensional representation. The three dimensional representation can include an animated three dimensional representation of the rescue scene. The one or more processors can be configured to determine an identity of the rescuer and select a profile associated with the rescuer based on the identity. The identity of the rescuer can be determined based on analyzing the images. The identity of the rescuer can be determined based on receiving an input from a user interface.

In yet another aspects, the real-time feedback can include at least one of an audio signal, a haptic signal, and a visual display. The visual display can include guidance to the rescuer for administering the CPR treatment. The guidance to the rescuer can include one or more images providing instruction of how to modify the body position of the rescuer. The haptic signal can be communicated to a haptic garment worn by the rescuer, the haptic garment can include one or more feedback devices configured to deliver haptic feedback to the rescuer wearing the garment. The one or more feedback devices can be configured to deliver haptic feedback to at least one of the arms, elbows, shoulders, hips and torso of the rescuer.

In yet another aspects, the real-time feedback to the rescuer indicates a modified position of the rescuer, the modified position representing a template position for the CPR treatment. The real-time feedback can be provided to instruct the rescuer to straighten elbows during a chest compression phase of CPR. The real-time feedback can be provided to instruct the rescuer to maintain shoulders above the sternum of the patient and hands of the rescuer. The real-time feedback can be provided to instruct the rescuer to fully release during a chest decompression phase of CPR.

In yet another aspects, the system can include one or more sensors attached to the rescuer and configured to sense one or more parameters representative of a fatigue level of the rescuer. The one or more processors can be in communication with the one or more sensors, and the one or more processors can be configured to analyze the one or more parameters to determine a fatigue level of the rescuer. The real-time feedback can be chosen based at least in part on the determined fatigue level of the rescuer. The one or more sensors can be configured to monitor at least one of ETCO2, SpO2, SmO2, a heart rate, a blood pressure, a muscle pH, and a lactate content.

In yet another aspects, the system can include: an electronic patient monitor, a set of patient sensors configured to sense one or more signals associated to the CPR treatment being provided, and a CPR monitor included in an electronic patient monitor and configured to use the input from the set of patient sensors to identify and display a quality level of the CPR treatment being provided. The electronic patient monitor can be a mobile device. The quality level of the CPR treatment can be used to determine the real-time feedback to the rescuer. The quality level of the CPR treatment reflects a depth of chest compressions, rate of compression, or both. The electronic patient monitor can be part of an external patient defibrillator. The one or more processors can be configured to transmit the fatigue level of the rescuer to a central management system. The one or more processors can be configured to transmit the fatigue level of the rescuer to other rescuers that can be attending to the patient.

In yet another aspects, analyzing the images to determine the body position of the rescuer can include processing data associated with visual markers attached to the rescuer. The camera can be mounted on the rescuer. The camera can be mounted on the patient. The one or more processors can be configured to communicate data to and from a wearable computing device that can include the camera. The camera can be mounted on a medical device proximate to the rescuer. The body position of the rescuer at a first time can be a first body position that corresponds to a first CPR phase and the body position of the rescuer at a second time can be a second body position that corresponds to a second CPR phase In another implementation, a wearable device that can be configured to provide haptic feedback to a rescuer performing a cardiopulmonary resuscitation (CPR) treatment to a patient in need of emergency assistance is disclosed. The wearable device can include: one or more processors configured to: receive a signal based on analyzed images of the rescuer, and based on the received signal, cause the wearable device to provide the haptic feedback to the rescuer to improve a manner, in which CPR treatment can be provided. The wearable device can include a camera, in communication with the one or more processors, configured to capture images of the rescuer performing the CPR treatment. The haptic feedback can be provided as an intermittent signal or as a continuous signal. The haptic feedback can be provided at one or more regions of the body of the rescuer at a time. The one or more regions can be aligned with at least one of arms, elbows, shoulders, hips and torso of the rescuer.

In one aspect, the one or more processors can be configured to receive images of the rescuer, analyze the images to determine a body position of the rescuer, and compare the body position to data representing a template position. The one or more processors can be configured to analyze the images to determine characteristics of a rescuer motion over one or more periods of time. The template positon can be selected based on data representing physical characteristics of the rescuer, wherein at least one of the physical characteristics can be relevant to an ability of the rescuer to perform the CPR treatment. A profile associated with the rescuer can include data representing physical characteristics of the rescuer, wherein the profile can be at least one of an expert profile, an intermediate profile, a novice profile, a default profile, and a profile that can be optimized for the given rescuer based off of previous testing/mock rescue attempts. The data representing physical characteristics of the rescuer can include data representing at least one of a body type, a time interval to fatigue and a history of training.

In other aspects, the one or more processors can be configured to analyze the images by generating a three dimensional representation of a rescue scene, the three dimensional representation can include a first representation of at least a portion of the rescuer and a second representation of at least a portion of the patient in need of emergency assistance by the rescuer. The three dimensional representation of the rescue scene can include removing information sufficient to identify the patient from the three dimensional representation. The three dimensional representation can include an animated three dimensional representation of the rescue scene. The one or more processors can be configured to determine an identity of the rescuer and select a profile associated with the rescuer based on the identity. The identity of the rescuer can be determined based on analyzing the images. The identity of the rescuer can be determined based on receiving an input from a user interface.

In yet another aspect, the real-time feedback can include at least one of an audio signal, a haptic signal, and a visual display. The visual display can include guidance to the rescuer for administering the CPR treatment. The guidance to the rescuer can include one or more images providing instruction of how to modify the body position of the rescuer. The haptic feedback to the rescuer indicates a modified position of the rescuer, the modified position representing a template position for the CPR treatment. The haptic feedback can be provided to instruct the rescuer to straighten elbows during a chest compression phase of CPR. The haptic feedback can be provided to instruct the rescuer to maintain shoulders above the sternum of the patient and hands of the rescuer. The haptic feedback can be provided to instruct the rescuer to fully release during a chest decompression phase of CPR.

In yet another aspect, the wearable device can include one or more sensors in communication with the one or more processors and configured to sense one or more parameters representative of a fatigue level of the rescuer. The one or more processors can be configured to analyze the one or more parameters to determine a fatigue level of the rescuer. The haptic feedback can be chosen based at least in part on the determined fatigue level of the rescuer. The one or more sensors can be configured to monitor at least one of ETCO2, SpO2, SmO2, a heart rate, a blood pressure, a muscle pH, and a lactate content. The wearable device can include a garment having a wearable body structure. The garment can include one or more active areas configured to provide the haptic feedback. The one or more active areas include a haptic substrate and a flexible material surface. The haptic substrate can include a surface-reconfigurable haptic element configured to change surface features of the haptic substrate in response to one or more activating signals. The one or more active areas can be configured to be aligned with a desired portion of rescuer anatomy. The wearable device can include a layer of high-traction or anti-slip material configured to maintain a contact between the one or more active areas and the desired portion of the rescuer anatomy that can be undisturbed by a movement of the rescuer during the CPR treatment.

Other features and advantages will be apparent from the description, from the drawings, and from the claims.

DESCRIPTION OF DRAWINGS

FIGS. 2A and 2B show frontal and perspective views of rescuers performing CPR correctly according to certain protocols.

DETAILED DESCRIPTION

Figure 1A:
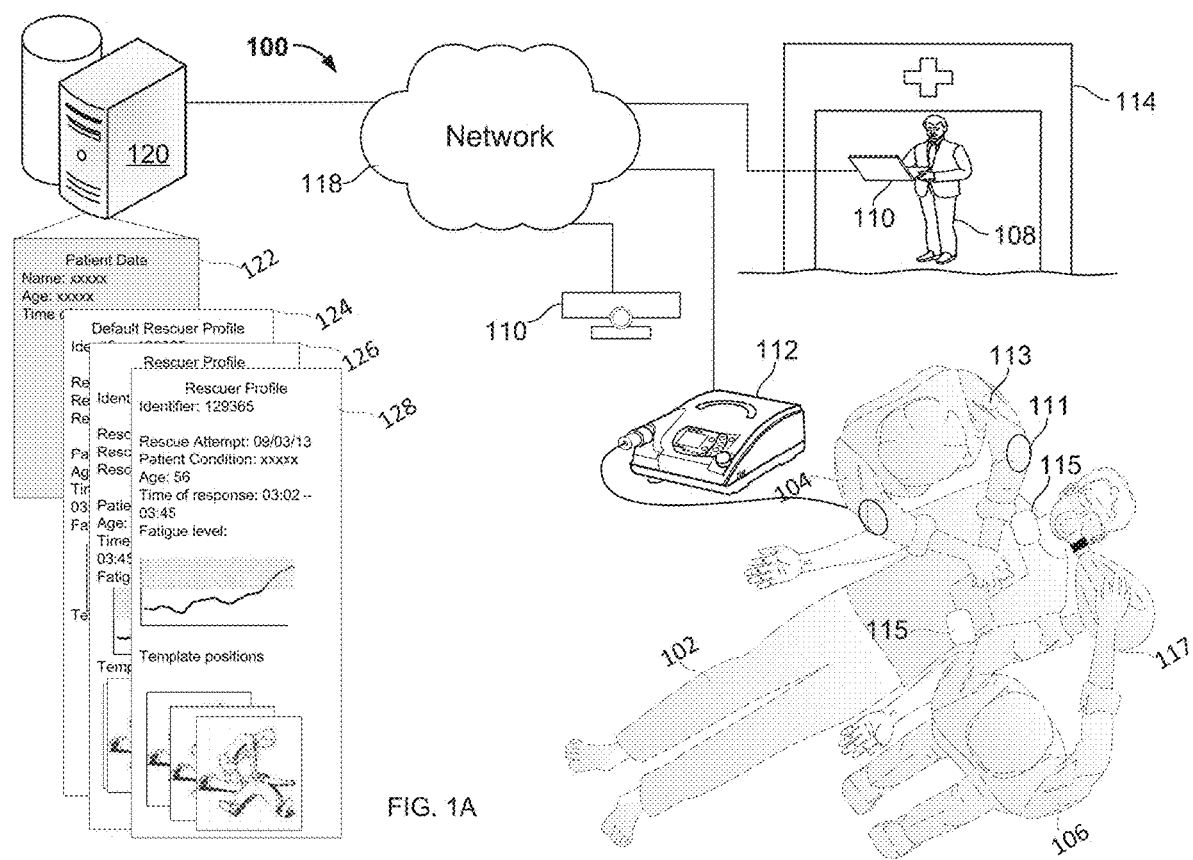
FIGS. 1A-1D show overhead views of rescuers providing resuscitative treatment to a patient using a CPR assistance system that includes cameras in different locations in accordance with certain embodiments.

Implementations of the present disclosure are generally directed to systems and techniques for real-time kinematic analysis during cardio-pulmonary resuscitation (CPR) of a patient suffering of cardiac arrest. For example, a system including a camera, feedback components (e.g., for visual, audio and/or haptic feedback), physiologic sensors, a puck (e.g., containing an accelerometer), and/or other suitable components can be provided to rescuers to provide real-time kinematic assistance during CPR. By "real-time," we mean that the assistance occurs during the CPR treatment for the purpose of improving the manner, in which CPR of the treatment is provided. The system can be a defibrillator that is provided with a mechanism for sensing the manner, such as a camera, in which CPR chest compressions are performed on the patient.

Embodiments described herein may involve a camera configured to capture images of a rescuer performing CPR treatment (e.g., chest compressions), and one or more processors configured to receive images of the rescuer and analyze the images to determine the body position of the rescuer while administering CPR treatment. The processor(s) may compare the body position of the rescuer to data representing a recommended template position. The processor(s) may further be configured to send a signal that results in real-time feedback being provided to the rescuer for improving the manner in which CPR is provided for the purpose of improving the overall outcome of the CPR treatment, based on the analyzed images as compared to the template position. Such feedback can be visual, audio and/or haptic in nature, provided by any suitable mechanism. In some embodiments, the rescuer can be using a wearable device configured to provide haptic feedback to the rescuer for adjusting certain aspects of the body position. For example, the wearable device may provide haptic feedback at a particular location that causes the wearer to adjust his/her position at that location, so as to provide higher quality CPR.

The processor(s) for analyzing the images of the rescuer can be located at any suitable location. For example, the processor(s) can be located on a defibrillator, tablet, monitor, mobile device, ventilator and/or any other device that is able to analyze the images of the rescuer and compare those images to a recommended template. Alternatively, the processor(s) for executing such analysis can be located on a wearable device used by the rescuer.

The system can use the information from such a sensor to identify a three-dimensional (3D) position of a rescuer, a depth, a rate of chest compressions that are being performed by the rescuer, and a 3D position of the patient. Also, the system can process internal factors of the rescuer such as pulse and blood oxygen level. The system can process a sequence of 3D positions of the rescuer and additional information to determine a sequence of desirable 3D positions, desirable body motions of the rescuer and to provide real-time feedback to optimize CPR treatment. The sequence of desirable 3D positions can be based on template body positions associated to a rescuer profile and adapted to one or more CPR conditions.

For example, in response to a determination that the 3D position of the rescuer is inadequate and/or chest compressions are inadequate, the system can provide a real-time indication to the rescuer to perform chest compressions according to an optimized protocol including alignment of rescuer position to a template position. In some implementations, the system provides a real-time personalized feedback to the rescuer. The personalized feedback can be based on a rescuer profile. The rescuer profile can be a default rescuer profile, a profile associated with one of a number of different rescuer types (e.g., based on age, height, weight, experience level, etc.), or a rescuer specific profile.

The rescuer profile includes a collection of template positions that are associated to particular characteristics of a rescuer that are relevant to CPR delivery. Such template positions can be collected under controlled test conditions (e.g., mock rescue attempts), during real CRP sessions and/or can be computer generated. The controlled test conditions can include having the user perform CPR on a standard foam training pad or a training dummy, while a camera records the body position and a processor measures the motion (e.g., acceleration and other motion data). The CPR sessions used to collect template positions can be any performed CPR sessions, during which the rescuer performance was monitored by a camera or they can be filtered such that only successful CPR sessions are used to extract template positions for either default rescuer profiles or rescuer specific profiles. Computer algorithms that generate rescuer positions can use a set of template positions that were recorded by a camera monitoring a rescuer. Such computer algorithms can extract the displacement of particular body parts of the rescuer during CPR and integrate such displacement in different body types (e.g., different body-mass indexes) to generate default rescuer profiles.

In some implementations, the collection and retrieval of a rescuer specific profile is based on corresponding rescuer data. The rescuer data can include a rescuer identifier, fitness related indicators, body postures, amplitudes of compression, success in CPR treatment, duration to fatigue, ability to respond to audio and video signals from the area around the test subject during CPR treatment and other data associated to CPR treatment. The collected rescuer data can be analyzed to determine if the rescuer performed satisfactorily under the applicable standards for CPR certification.

The analysis can also be used to categorize and/or update the skill level of the rescuer to save it under the rescuer specific profile. The skill level can also be associated with a total number of CPR treatments and/or CPR training sessions performed by a particular rescuer and the time that passed since the last treatment was performed. The data associated to a rescuer specific profile can be collected multiple times to repeat the analysis of the rescuer's performance under multiple conditions and/or to determine the variation of the CPR treatment skill level. Based on the skill level, any of the default rescuer profile and the rescuer specific profile can include an expert profile, an intermediate profile, a novice profile, a beginner profile and/or other profiles optionally based on other characteristics, such as rescuer size.

In some implementations, any of the default rescuer profile and the rescuer specific profile can be optimized based on one or more conditions by using data from previous testing/mock rescue attempts. The optimization of the rescuer profile can be designed to improve a manner, in which CRP treatment is provided (e.g., by preventing premature fatigue of the rescuer), as described in detail with reference to FIGS. 1A-1D, 10A, and 10B.

FIGS. 1A-1D show examples of a system 100 for responding to an emergency medical condition of a patient 102 by providing CPR. FIGS. 1A-1D illustrate overhead views of rescuers 104,106 performing CPR on the patient 102 using an electronic system that instructs them in performance of the CPR based on a rescuer profile.

In the illustrated example, the rescuers 104 and 106 are already in position and providing care to the patient 102, with rescuer 104 in position and providing chest compressions to the torso of the patient 102, and rescuer 106 providing ventilation using a ventilation bag 107. The rescuers 104 and 106 can be lay rescuers who were in the vicinity of the patient 102 when the patient 102 required care, or can be trained medical personnel, such as emergency medical personnel (EMTs). Although two rescuers are shown in FIGS. 1A-1D, additional rescuers can also care for the patient 102, and can be included in a rotation of rescuers providing particular components of care to the patient 102, where the components can include chest compressions, ventilation, administration of drugs, and other provisions of care.

In general, the system 100 includes various portable devices for monitoring on-site care given to the patient 102. The various devices can be provided by emergency medical personnel who arrive at the scene and who provide care for the patient 102, such as rescuers 104 and 106. The onsite rescuers 104 and 106 can be assisted by remote medical personnel 108, located at a medical facility 114 within a healthcare continuum. In the illustrated example, the rescuers 104 and 106 use several devices to provide an emergency treatment to the patient 102.

Figure 1B:
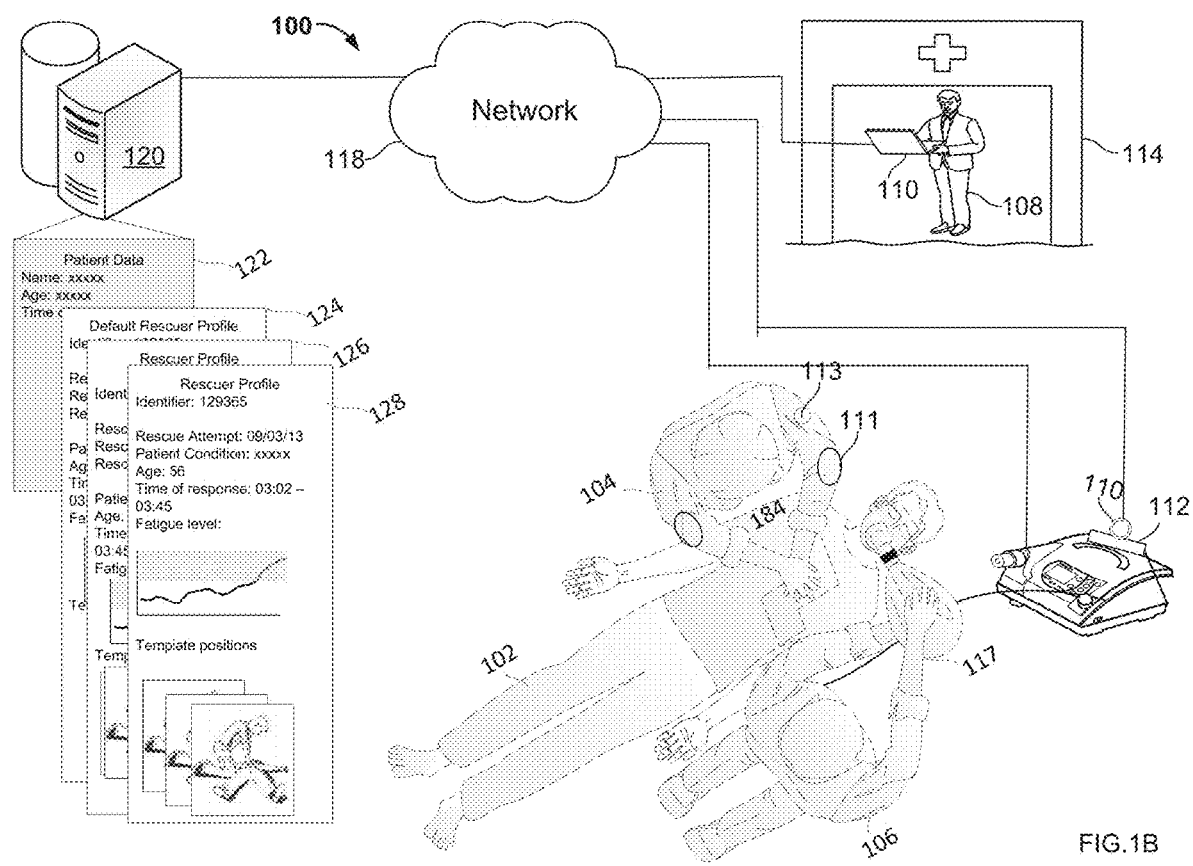
Figure 1C:
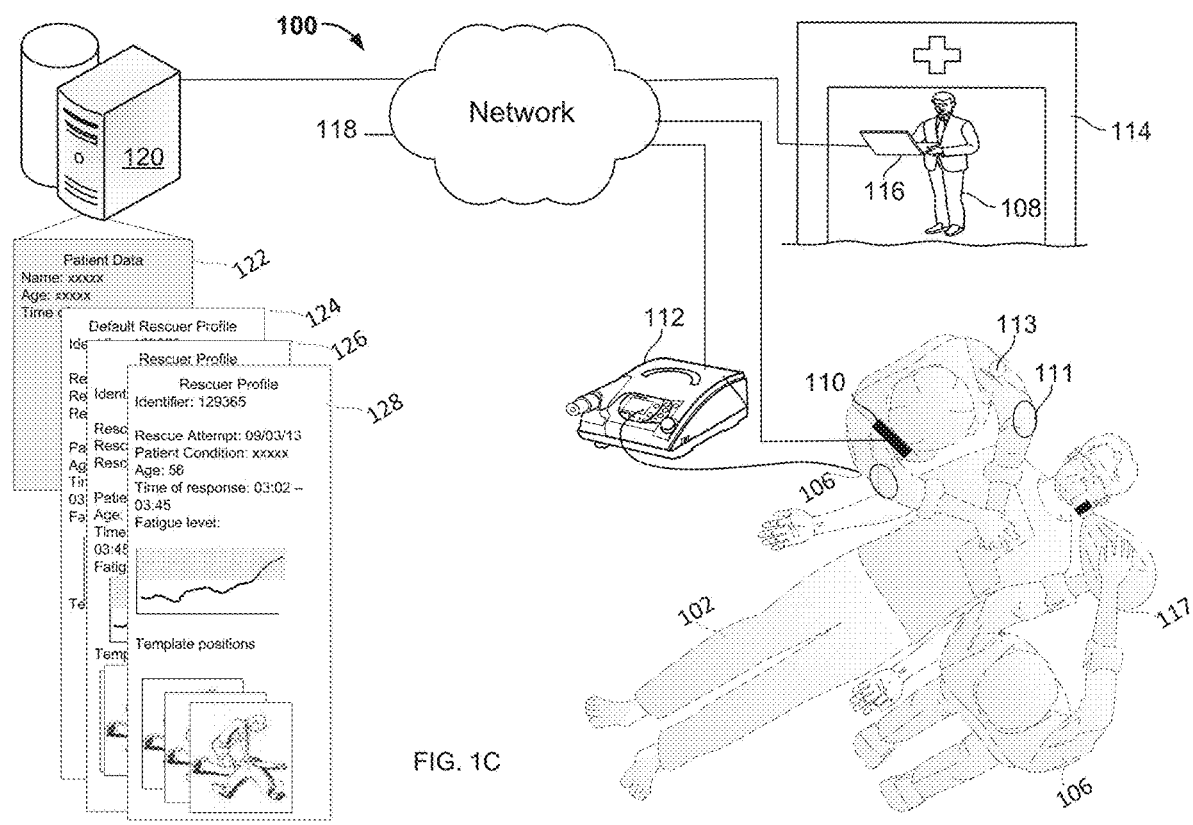
Figure 1D:
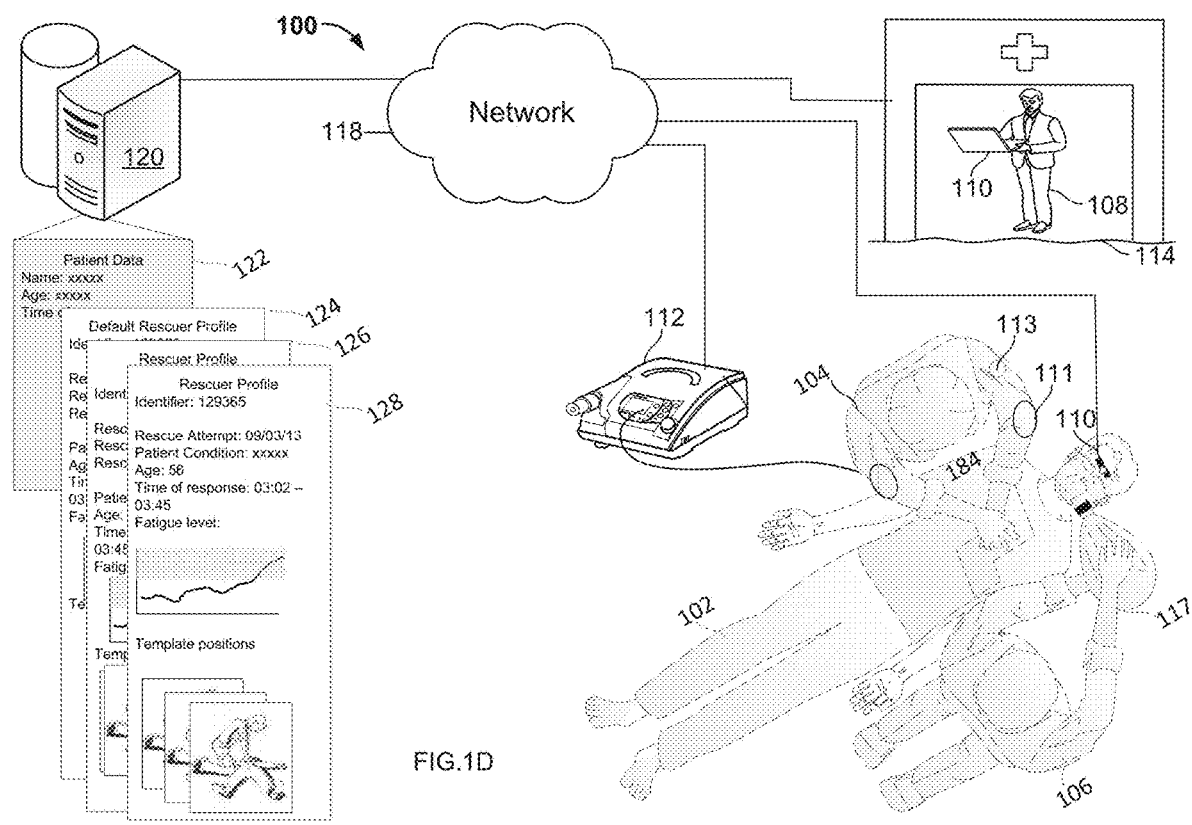

The devices used by the rescuers 104, 106, and/or the medical personnel 108 during CPR can include a camera 110 and a portable defibrillator 112. The camera 110 can be a standalone device that is placed in the proximity of the rescue scene (as illustrated in FIG. 1A). For example, the camera 110 can be in a location where it can monitor the 3D position of the rescuer performing chest compressions (e.g., rescuer 106). The camera 110 can also be attached to another device used by the medical personnel during CPR, such as the portable defibrillator 112, as illustrated in FIG. 1B. The camera 110 can also be attached to one of the medical personnel performing chest compressions (e.g., rescuer 106), as illustrated in FIG. 1C. Or, the camera 110 can be attached to one of the medical personnel facing the rescuer that is performing the chest compressions. This way, the kinematic behavior of the rescuer performing the chest compressions can be easily visualized and recorded. The camera 110 can also be attached to the patient 102 (e.g., to the forehead of the patient 102), as illustrated in FIG. 1D. The camera 110 may also be placed on the ventilation bag, or component thereof. When placed on the patient, the camera 110 can be capable of recording a relatively wide panoramic field (e.g., 180 degrees, 360 degrees around the patient), so that rescuer position can be fully and accurately captured.

In some implementations, the rescuer performing chest compressions (e.g., rescuer 106) has one or more markers 111 attached to the body that improve the detection of the position with the camera 110. The rescuer performing chest compressions (e.g., rescuer 106) can also have one or more sensors 113 attached to the body that detect the changes in position and/or data associated to fatigue level. Or, in some embodiments, the camera can be configured to project a grid of markers so as to capture high resolution rescuer motion. For example, a camera using technology similar to that of the Kinect motion sensing input device provided by Microsoft Corporation can be employed. Such cameras may include a depth sensor employing an infrared laser projector combined with a monochrome CMOS sensor which allows for 3D video data to be captured under ambient light conditions. It can be appreciated that any suitable video imaging systems can be used. A three-dimensional representation can be generated by a 3D surface imaging technology with anatomical integrity, for instance the 3dMDthorax System (3dMD LLC, Atlanta Ga.).

In FIGS. 1A-1D, single cameras are shown. However, system 100 can also include multiple cameras, including any possible combination of the cameras illustrated in FIGS. 1A-1D and other cameras. In some implementations, the camera 110 can be placed in a particular location by one of the rescuers 104, 106. The camera 110 can be battery-operated and can communicate with a central controller such as a controller in defibrillator 112 (see FIG. 1B). This camera 110 can be directional and can be aimed over the torso of the patient 102 so as to continuously capture the position of the rescuer 104 with respect to the patient 102 during CPR treatment. The camera 110 can also show who is currently providing ventilation to patient 102 and who is providing chest compressions. The camera 110 can also be a 360 degree camera that captures 3D images through a dome in a standard manner.

In some examples, the camera 110 can be attached to or integrated with electronic glasses worn by rescuers 104 and 106, respectively. These cameras can be forward facing so as to have a field of view that approximates a field of view of the respective rescuer. In some examples, in addition to capturing and transmitting images form the scene, the glasses can perform a variety of different functions, including having a microphone by which a rescuer can communicate with other rescuers, with a dispatcher, and/or with a remotely located physician who is going to receive the patient 102 when the rescuers get to a hospital emergency room. In some examples, the glasses can also provide heads-up displays that appear to be in front of the respective rescuer and that show optimized rescuer positions in real-time, vital signs of the patient 102, information that is also displayed on a visual display of the defibrillator 112, instructions for treating the patient obtained from a remote database, and other such information that includes real-time status information about the CPR treatment. The glasses can take the form, for example, of the Google Glass computing glasses.

The glasses may also take the form of other head-mounted displays such as the Microsoft Hololens®. The head-mounted displays may incorporate virtual reality (VR) support so that the rescuer can see a three-dimensional, VR image overlaid onto his own elbows or other body parts, showing the correct positioning and orientation of the rescuer's joints. The 3D VR instructional images can have specific joints and body elements that are visually highlighted to indicate what the rescuer needs to change about both the static and dynamic performance of his chest compressions. For instance, the positional and dynamic feedback might begin with the rescuer positioning their hands and body in preparation for doing a chest compression. The system would provide visual, auditory or verbal feedback of whether the rescuer's hands are positioned correctly, whether their shoulders, hips and head are positioned correctly, and in some embodiments whether, based on these static criteria, it is ok for the rescuer to begin compressions. Then, while compressions are beginning, standard chest compression rate, depth release feedback can be provided (this "standard", commercially available chest compression feedback can be found in defibrillators manufactured by ZOLL Medical Chelmsford Mass.). Once these standard parameters are within an acceptable range, then more advanced feedback can be provided dynamically. This advanced feedback may entail feedback of body position, as described above, or may entail more subtle aspects like how the rescuer is using his elbows during the chest decompression and release phase, e.g. straight or bent elbows.

One or more cameras can also be included in a medical equipment. For example, defibrillator 112 can be provided with a camera attached to its front or top, where the camera has a large aperture of the field of view in front of the defibrillator 112. Typically, the defibrillator 112 can be oriented toward a rescuer 104 or 106 who wants to see and/or interact with a display of the defibrillator 112, and thus will have a front field of view that includes the patient and the rescuers.

Any of the cameras, and particularly those attached to relatively stable items such as the patient, a medical device, or an ambulance, can have self-aiming mechanisms included in the cameras. In particular, the cameras can scan either electronically through a field of view or mechanically to capture a new field of view, until a processor receiving data form a particular camera senses motion or items indicative of a patient being treated. Software receiving the images can be programmed to scan until an image is captured that matches a signature of a patient being treated, such as a horizontal patient at ground level and moving items (rescuers) around the horizontal object. Similarly, a camera mount at the back of an ambulance can scan an area for items and motion indicative of rescue operations on a patient. Such scanning can also be performed in combination with other location techniques, such as using triangulation to roughly identify where rescuers are located, and using image and motion recognition to more finely identify the rescuers.

The detection of 2D or 3D images and other data form a rescue scene can be coordinated between and among the various devices on a scene so that all of the data can be combined in a manner that aligns it all time-wise with each other. For example, if the system is determined to have minimum latency, each of the devices can simply stream data in real-time to a central system (e.g., a computer system in a nearby ambulance) and that system can assemble the parts into an overall data transcript of an event. Alternatively, each device can keep a coordinated timeline with the data it collects, so that even if there is delay in transmitting the data to a common hub, that common hub can assemble all of the disparate pieces of data from different devices using the timeline as a base for aligning data. The coordination can occur, for example, by a central unit periodically transmitting a coordination signal that all other devices listen to, or by a mesh approach in which each device communicates with a nearby device so as to coordinate timing information that can be used to align events in a single event log that captures all data from the event.

As previously noted, one or more of the cameras can have a 360 degree field of view and/or can be a light-field camera that permits post-capture identification of a focus distance for an image (which can be a single image or a sequence of images, such as a video). The light field cameras can permit humans or software that are reviewing the captured video to "zoom in" +on particular items in the field of view of the camera. For example, if text is identified in an image, the focus can be applied to that text after the image is captured so as to make the text clearer and to enable superior optical character recognition of the text. Alternatively, when two rescuers 104 and 106 are located at two substantial different distances form the camera, the post-processing can be used to focus on one or the other of the rescuers. Such post-focusing can be performed manually in response to inputs from a user reviewing the images (e.g., watching a video or a rescue) or automatically, such as software identifying something of interest in the image (e.g., torso of the rescuer 104 performing chest compressions and at least a portion of the body of the patient 102) and then focusing to that field of view.

Locations of objects in a scene (e.g., a patient, rescuers, and other items) can be identified at least in part by performing differential focus analysis on light-field camera images. In particular, the characteristics of a light field camera can be known, and the distance of an objective from the camera can be determined by identifying when it is in or out of focus under different post-processing settings of the software for analyzing light-field captured images. Such information can be combined, for example, with laser capture data of a scene (where the laser source is in or with one or more of the cameras or a separate location such as a high point on a rescue vehicle, where the laser scans an area, and a 3D model of the area can be created by such scanning. Also, the data can be combined with analysis of images taken from different angles, and the positions of rescuers 104 and 106 can be identified by the relationship of the images they are capturing as compared to the images captured by other cameras.

The light field camera 110 can also be used to measure the depth and rate of compressions and be used to assess the performance of rescuers and initiate a switch of rescuer performing compressions, in manners like those discussed above. As one example, the light field camera 110 can be used to measure the patient's chest size and/or other patient size information (e.g., height, weight, etc.) and use the data to adjust compression quality goals. Or, such information can be input into the system, for example, via a user interface. The light field camera 110 can also be used to analyze the movement of the rescuer and that data can be used to give more specific instructions to rescuers for example "release compressions fully" or "keep arms straight." The light field camera 110 can also be used to identify the position of individual rescuers and equipment, and the image data collected can be used to create three dimensional views of the rescue. Such analysis and identification can be performed, for example, by a system that receives image information recorded by the camera, such as a defibrillator, monitor, administrative computer, tablet, etc.

Standard sensor packages like those found in smartphones can also be arranged to move with each of the cameras. For example, a sensor pack can include an accelerometer, an inclinometer, a magnetometer, and the like. Such sensors can be used to identify the orientation and position of each camera, and to thereby better identify what the camera is showing. For example, if the patient camera 110 is set with no incline (and is showing human movement in its field of view), it might be inferred that the camera is pointing horizontally straight down the torso of the lying patient 102.

Image data can be used to provide real-time feedback to optimize CPR treatment, as described with reference to FIG. 10. For example, it can be determined that rescuer's position is significantly different from standard CPR protocol. Such information can be identified from video taken by the patient-mounted camera 110 or by movement of the image in additional cameras or movement sense by sensor packs in the camera 110. A display of the defibrillator 112 can assist the rescuer to correct the position and align it according to the CPR protocol.

In addition to the camera 110, FIGS. 1A-1D show a portable defibrillator 112 and ancillary components arranged to provide feedback and instruction to rescuers. Each of the figures shows an example, in which visual feedback can be provided to a rescuer from a location that is away from the defibrillator unit, and more immediately in the line of sight and focus of attention of a rescuer, such as a rescuer who is providing CPR chest compressions.

The portable defibrillator 112 is shown in a deployed state and is connected to the patient 102. In addition to providing defibrillation, the defibrillator 112 can serve as a patient monitor via a variety of sensors or sensor packages. For example, as shown here, electrodes 115 have been applied to the bare chest of the patient 102 and have been connected to the defibrillator 112, so that electrical shocking pulses can be provided to the electrodes in an effort to defibrillate the patient 102, and electrocardiogram (ECG) signals can be read from the patient 102. The defibrillator 112 can provide feedback in a conventional and known manner to an onsite rescuer, such as emergency medical personnel 104 and 106.

In some implementations, additional therapeutic delivery devices (not shown) can be used to deliver the appropriate therapy to the patient. The therapeutic delivery devices can be, for example, a drug infusion device, an automatic ventilator and/or a device that includes multiple therapies such as defibrillation, chest compression, ventilation, and drug infusion. The therapeutic delivery devices are physically separate from the defibrillator 112, and control of the therapeutic delivery devices can be accomplished by a communications link from the defibrillator 112 that can be wired, wireless, or both.

In some implementations, control and coordination for the overall resuscitation treatment and the delivery of the various therapies can be accomplished through optimized chest compressions based on rescuer's profile by a processor that is integrated in the defibrillator 112 or is external to the defibrillator 112, such as the computing device 116 that is controlled by remote medical personnel 108. For instance, the computing device 116 can retrieve and process 3D position of the rescuer 104, ECG data from the defibrillator 112. The computing device 116 can analyze the 3D position of the rescuer 104 based on a profile of the rescuer 106. In parallel with analyzing the position of the rescuer 104 it can process ECG signals, and perform relevant determinations to optimize the position of the rescuer and therefore increase the success of CPR. In some implementations, the processor integrated in the defibrillator 112 can perform all the processing of the position of the rescuer 104 and the ECG, and can display a suitable level of feedback to the rescuers 104 and 106. The defibrillator 112 can also transmit to a separate device particular sets of processed data, and in response, the separate device can perform particular control actions.

An electrode assembly 115 is illustrated as being attached to the patient 102 in a standard position. The electrode assembly 115, in this example, is an assembly that combines an electrode positioned high on the right side of the patient's torso and an electrode positioned low on the left side of the patient's torso, along with a sensor package located over the patient's sternum. The sensor package, which is obscured in the figure by the hands of rescuer 104 in this example, can include an accelerometer or similar sensor package that can be used in cooperation with a computer in the defibrillator 112 to generate an overall quality score for the chest compression, and the quality score can indicate instantaneous quality or average quality across a time. For example, as a simplified description, signals from an accelerometer can be double integrated to identify a vertical displacement of the sensor package, and in turn of the sternum of the patient 102, to identify how deep each chest compression is. The time between receiving such input from the sensor package can be used to identify the pace at which chest compressions are being applied to the patient 102.

The defibrillator 112 in this example is connected to the electrode package 115 and can operate according to standard protocol (e.g., to provide defibrillating shocks to the electrode package 115). The defibrillator can be a professional defibrillator, such as the R SERIES, M SERIES, E SERIES, or X SERIES from ZOLL Medical Corporation of Chelmsford, Mass., or an automated external defibrillator (AED), including the AED PLUS, or AED PRO from ZOLL Medical Corporation. The defibrillator is shown in one position relative to the rescuers 104 and 106 here, but can be placed in other locations to better present information to them, such as in the form of lights, displays, vibrators, or audible sound generators on a chest-mounted component such as an electrode or via an addressable earpiece for each of the rescuers. Such feedback, as discussed more fully below, can be on units that are separate from the main housing of the defibrillator, and that can communication information about the patient 102 and performance of CPR to the defibrillator 112 or can receive feedback information from the defibrillator 112, through either wired or wireless connects that are made directly with the defibrillator 112 or indirectly through another device or devices.

In some implementations, the camera 110 and the defibrillator 112 can be connected to the network 118 to transmit the acquired data to a computing device 116 that can be operated by the remote medical personnel 108. The CPR data transmitted by the camera 110 and the defibrillator 112 to the computing device 116 can include data associated to rescuer performance and data associated to the response of the patient 102 to CPR. The camera 110 can send information that includes the position of the rescuer and information about the fatigue level of the rescuer (e.g., as described herein). The defibrillator 112 can send ECG data and information about the performance of chest compressions, such as depth and rate information for the chest compressions. The computing device 116 can also receive data from the other sensors associated with the patient 102 such as an airflow sensor attached to a ventilation bag 107.

A central server system 120 can communicate with the computing device 116 or other devices at the rescue scene over a wireless network and/or a network 118, which can include portions of the Internet (where data can be appropriately encrypted to protect privacy). The central server system 120 can be provided as a server, or a virtual server, that runs server software components, and can include data storage including, but not limited to, a database and/or flat files. The central server system 120 can be part of a larger system of a healthcare continuum, in which patient data 122 and rescuer profiles 124, 126, and 128 are stored. Patient data 102 can be associated with an identification number or other identifier, and stored by the central server system 120 for later access.

Additionally, the central server system 120 can store rescuer profiles 124, 126, and 128 that include default rescuer profiles 124 and rescuer specific profiles 126 and 128 associated with particular rescuers. A rescuer specific profile associated with a particular rescuer can be retrieved by using an identification number or other identifier, stored by the central server system 120 for later access. The rescuer specific profiles 126 and 128 can include template positions and data extracted from past rescue attempts, in which the rescuers participated. The data extracted from past rescue attempts can include rescuer's performance during CPR. The rescuer's performance during CPR can include rescuer's skill level in performing CPR treatment, indicators of rescuer fatigue level, duration of CPR, and success of CPR treatment.

Users interacting with the system 100 can access the data in the central server system 120. For example, as shown in FIGS. 1A-1D, medical personnel 108, operating a computing device 116 that communicates wirelessly, such as over a cellular data network can access current and past CPR data. As such, the medical personnel 108 can review CPR data stored in the central server system 120. In this manner, the system 100 permits various portable electronic devices to communicate with each other so as to coordinate and optimize care that is provided to a patient 102 based on the profile of the available rescuers 104 and 106 at the rescue scene. In some examples, the rescuer specific profile 126 of the rescuer 104 indicates an expert level and the rescuer specific profile 128 of the rescuer 106 indicates a beginner/novice level. In such examples, the system 100 could be configured to optimize CPR treatment by preventing fatigue in rescuer 104, so that rescuer 104 can perform all chest compressions. In some examples, the rescuer specific profiles 126 and 128 of both rescuers 104 and 106 indicate expert/intermediate levels. In such examples, the system 100 could be configured to optimize CPR treatment by providing optimal chest compressions for shorter periods of time than the complete CPR duration and identification of the optimal moment for switching between rescuers 104 and 106 based on fatigue levels. In addition, the system 100 allows the rescuers 104 and 106 and other medical personnel to access real-time data and optimized real-time and/or historical data associated with a CPR treatment.

Example system 100 can provide real-time feedback to the rescuers 104 and 106. For example, the defibrillator 112 or a display of a computing device can provide real-time audio-visual and haptic feedback to the rescuers 104 and 106, as described in detail with reference to FIGS. 6A and 6B. The process of observing the quality of a component of the CPR, such as the quality of chest compressions, can continue recursively as long as care is being provided to the patient 102. In some implementations, trends in the quality of a particular CPR component can be tracked rather than absolute values of the performance, so that the defibrillator 112 can distinguish situations, in which a rescuer is giving poor chest compressions because he or she was trying to find the appropriate rhythm or was distracted by a temporary problem, from situations in which the user truly is tiring and rescuer's position should be optimized.

In some instances, the defibrillator 112 can be adaptable to different CPR protocols. For example, the defibrillator 112 can be programmed according to a protocol that, among other parameters, calls for multiple rescuers to provide chest compressions for a preset period of time. In such a situation, the defibrillator 112 can use pauses in the provision of chest compressions to determine when users have switched providing chest compressions, and can automatically update the rescuer's profile and start a timer based on such an indication. When the timer hits the preset period, the defibrillator 112 can then provide an indication that the rescuer giving chest compressions is to change. The timer can then be reset once next rescuer is identified as having started giving chest compressions, such as by recognizing a pause in the provision of chest compressions.

Other protocols can be more flexible and can allow switches in rescuers to be dependent on the performance of the rescuers in addition to a predefined time interval. For example, the defibrillator 112 can be programmed to indicate that rescuers should change when it senses that the rescuer fails at maintaining the template position or fails at matching the body position to the recommended body position. The defibrillator 112 can also indicate the need for change when a maximum preset time has occurred even if the current rescuer appears to have performed well. In such a protocol, the time interval can be substantially longer than an interval for a protocol that requires changing based only upon elapsed time, and not upon degraded performance by the rescuer. Various different protocols can call for changing of rescuers based on different levels in performance, or upon different elapsed time periods, or a combination of the two. In particular, AHA protocols are generally guidelines, and a particular medical director can alter such guidelines to fit their particular needs or professional judgment.

In such a situation, the defibrillator 112 can be programmed with the parameters for each of the protocols, and an operator of the defibrillator 112 can select a protocol to be executed by the defibrillator 112 (or the protocol can have been selected by a medical director). Such a selection can occur at the time of a rescue, or at a prior time. For example, the ability to select a protocol can be differentiated based on access privileges, such as a person who runs an EMT service (e.g., a medical director of appropriate training and certification to make such a determination). A user interacting with the defibrillator 112 can select the protocol to be followed on each of the machines operated by the service, and other users can be prevented from making particular changes, if lacking access privileges. In this manner, the defibrillator 112 can be caused to match its performance to whatever protocol its users have been trained to.

Thus, using the techniques described here, the defibrillator 112 can, in addition to providing defibrillation shocks, ECG analysis, and other features traditionally provided by a defibrillator, also provide indications to optimize the position of the rescuer in real-time and/or to switch rescuers between various components of providing CPR and other care to a patient. The defibrillator can be deployed in the same manner as existing defibrillators, but can provide additional functionality in a manner that can be easily understood by trained and untrained rescuers.

Figure 2A:
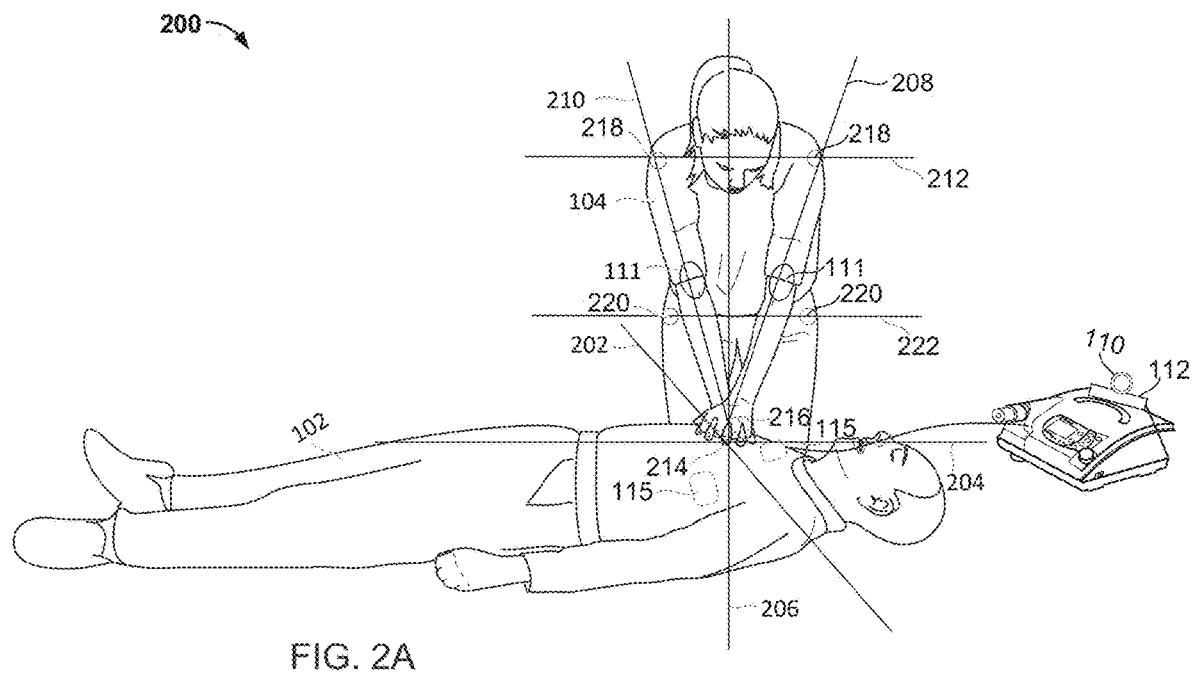
Figure 2C:
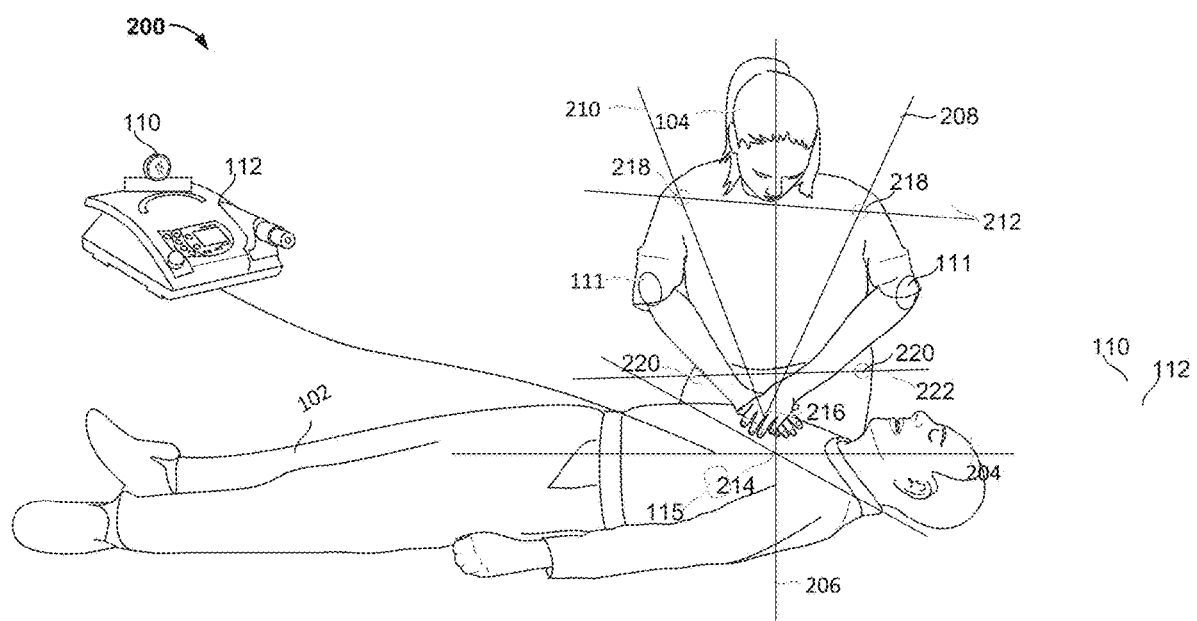
FIGS. 2C and 2D show frontal and perspective views of rescuers performing CPR incorrectly according to certain protocols.
Figure 2D:
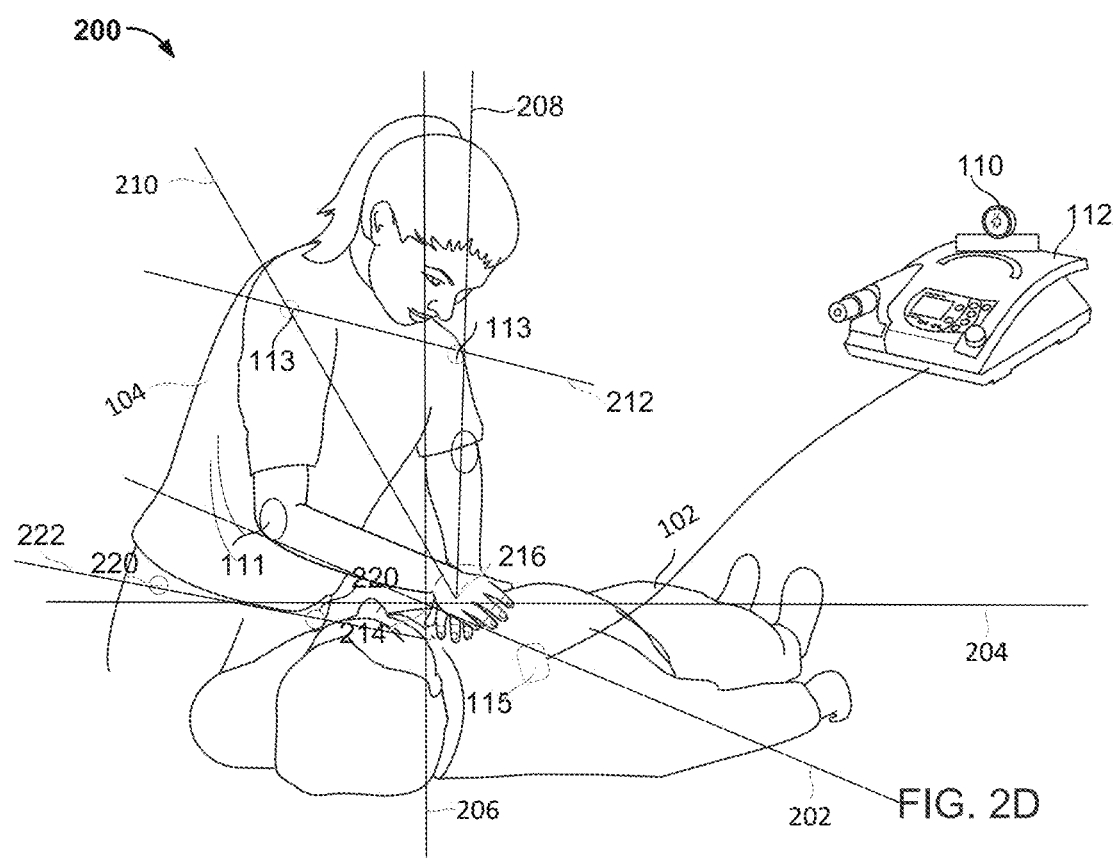

FIGS. 2A and 2B show frontal and perspective views of rescuers performing CPR correctly according to an example CPR protocol. FIGS. 2C and 2D show frontal and perspective views of rescuers performing CPR incorrectly according to the example CPR protocol. In some implementations, CPR protocol is a protocol approved at an international level, at a national level, by a healthcare continuum including multiple medical facilities, by a medical facility or by a user of the example system 200. In some implementations, the protocol can include a definition or recommendation of a correct position of the patient and a definition or recommendation of a correct position of the rescuer. The protocol may further provide a recommendation of orientation and motion of the rescuer relative to the patient. Accordingly, the recommended correct position of the patient can include a supine position (e.g., patient laying on his or her back on a firm flat surface). The recommended correct position of the rescuer can include a position type, a location and a body configuration. For example, a CPR protocol can recommend a correct position type as being a kneeling position. A correct location of the rescuer can be defined relative to the patient (e.g., rescuer kneeling near to the patient's neck and shoulders). The recommended correct body configuration can include a definition of multiple body points of the rescuer (e.g., hands, hips, shoulders and elbows) relative to multiple body points of the patient (e.g., chest and nipples). In some implementations, the correct body configuration of the rescuer can be defined as having the heel of one hand over the center of the patient's chest, between the nipples; having the other hand on top of the first hand; keeping the elbows straight; keeping the back straight; and positioning the shoulders directly above the hands.

The processor can also be configured to compare a rescuer position to an optimal rescuer position that was selected based on the rescuer profile. In some examples, the optimal position of a rescuer may vary depending on a rescuer's physical characteristics such as body size, physical fitness, etc. The data of the profile can be generated taking into account these characteristics, whether they are specific to the rescuer or specific to a general classification of the rescuer (e.g., CPR experience level, body weight class, etc.) For example, physical data associated to the rescuer can be used to match a stored physical model (as described in detail with reference to FIG. 10). In some implementations, the processor (e.g., integrated in defibrillator 112) is configured to process the images acquired by the camera 110 to identify multiple body points of the patient and the rescuer. The multiple body points of the patient and the rescuer can be identified through markers (e.g., elbow markers 111, shoulder markers 218, and hip markers 220). In some implementations, the multiple body points of the patient and the rescuer can be identified automatically by using feature and pattern recognition algorithms. In some implementations, the multiple body points of the patient and the rescuer can be manually identified by a user of the system 200 and automatically tracked during CPR treatment by using displacement tracking algorithms.

As illustrated in FIGS. 2A-2D, the processor can use one or more systems of coordinates for identifying multiple body points of the patient and the rescuer. A first system of coordinates can include orthogonal axes 202, 204, and 206, which are intersecting in the center of the patient's chest (e.g., point 214), between the nipples (point 214). In some implementations, two axes (e.g., horizontal axes 202 and 204) of the first system of coordinates can be used to identify whether the patient is in a correct supine position. In a second system of coordinates, a set of axes (e.g., axes 208, 210, and 212) can be used to define a triangle associated to the rescuer's body. The triangle could be formed from a side (e.g., axis 212) that intersects the shoulders (e.g., markers 218) of the rescuer and two sides (e.g., axes 208 and 210) that intersect the overlapping hands of the rescuer (e.g., point 216) and the shoulders (e.g., markers 218). In an example of a correct rescuer position (FIGS. 2A and 2B), the triangle associated with the rescuer's position is an isosceles triangle and the elbows intersect the sides of equal length (e.g., axes 208 and 210). In some implementations, an axis 222 intersecting the hip markers 220 can be used to analyze to position of the rescuer. In an example of a correct patient position and rescuer position (FIGS. 2A and 2B), axis 222 is parallel to axis 212 and to the plane formed by axes 202 and 204.

In an example of an incorrect rescuer position (FIGS. 2C and 2D), the triangle associated with the rescuer's position is a scalene triangle and the axis 212 that intersects the shoulders (e.g., markers 218) or the axis 222 is not parallel to the plane defined by the horizontal axes 202 and 204. In another example of an incorrect rescuer position (FIGS. 2C and 2D) one or both elbows (e.g., markers 111) do not intersect the sides (e.g., axes 208 and 210) that intersect the hands (e.g., point 216) and the shoulders (e.g., markers 218). In another example of an incorrect rescuer position (FIGS. 2C and 2D) one or both hands of the rescuer (e.g., point 216) do not overlap the center of the patient's chest (e.g., point 214).

Figure 3A:
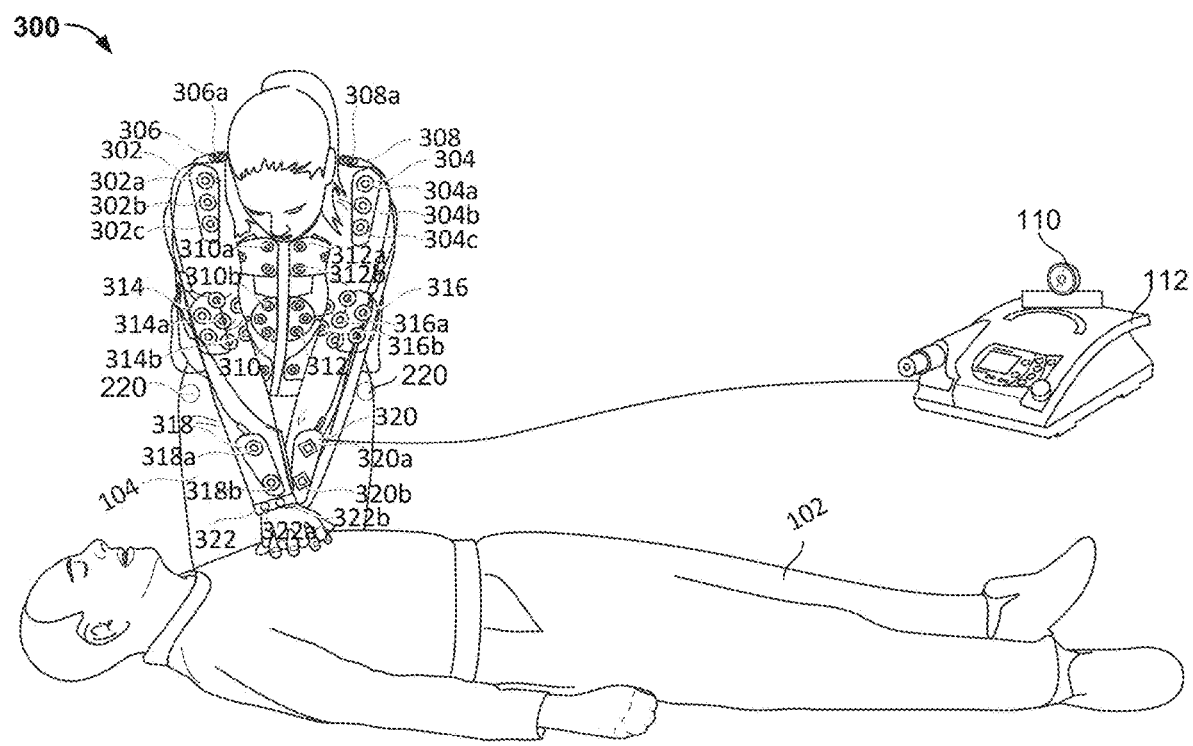
FIGS. 3A and 3B show frontal and perspective views of rescuers performing CPR while wearing a haptic garment in accordance with certain embodiments.
Figure 3B:
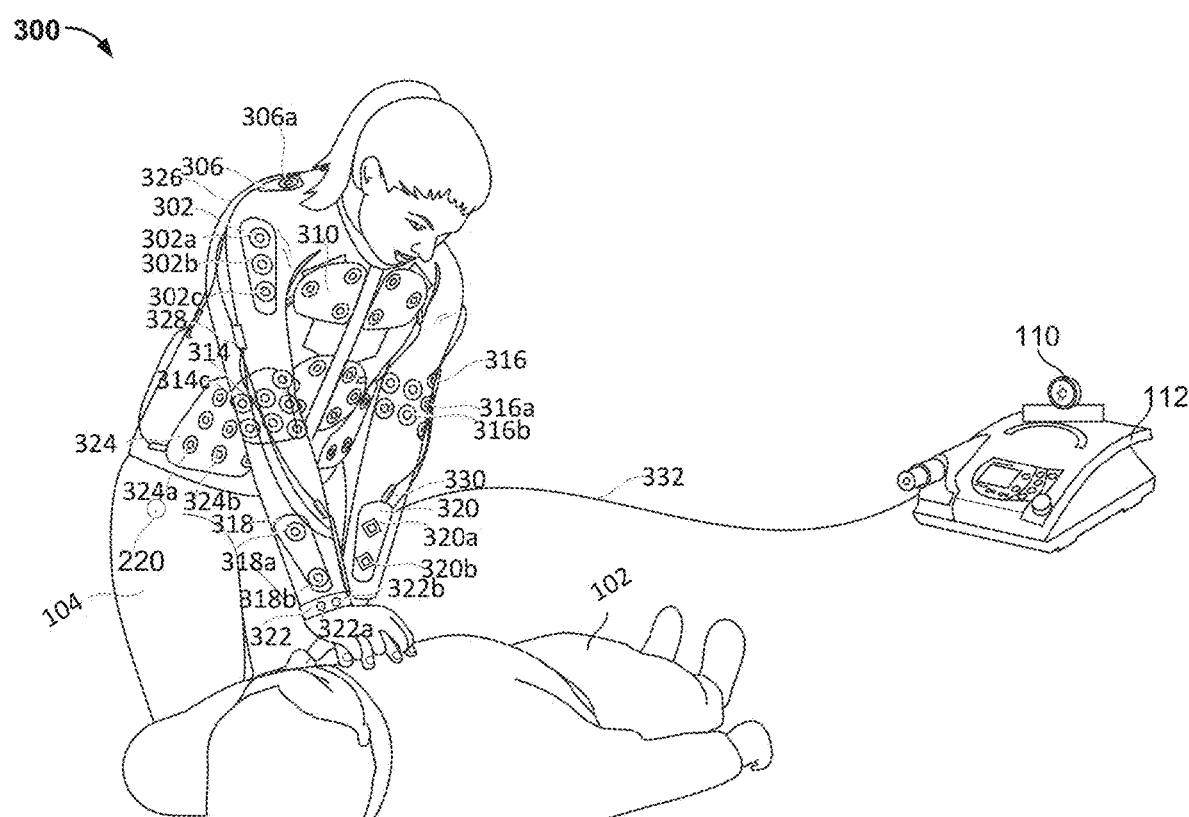

FIGS. 3A and 3B show frontal and perspective views of rescuers wearing an example of a garment 300 configured for assisting CPR in real-time. In some implementations, the garment 300 is configured to unobtrusively measure bioelectric signals of the rescuer 104, to provide haptic feedback and/or to enhance an image detection of the rescuer position with a camera 110. The garment 300 includes a plurality of active areas, such as shoulder active areas 302 and 304, back active areas 306 and 308, front active areas 310 and 312, elbow active areas 314 and 316, and wrist active areas 318, 320, and 322. Each active area 302-322 can be permanently or removably attached to the garment 300. An example of a removably attached active area can be an elastic band, which is held within a shirt. In some implementations, each active area can be both horizontally and vertically adjustable within the garment 300 through particular fitting features, such as snaps, Velcro, patches, elastic cords and toggle systems. With this arrangement, a rescuer, regardless of his or her size, only needs to put on the garment 300 and adjust the position of the active areas 302-322 by using the fitting features. In some implementations, garment 300 includes a stretchable fabric that automatically adjusts the position of the active areas 302-322 to a size of a rescuer 104.

One or more of the active areas 302-322 include one or more sensors that enable collection of physiological signals of the rescuer 104. The physiological signals of the rescuer 104 collected by the sensors can be associated to a fatigue level of the rescuer 104. For example, the sensor can be configured to acquire noninvasive indicators of fatigue level, such as lactate content, muscle pH, oxygen level, temperature or other physiological data that can be used for an evaluation of CPR performance.

In some implementations, the sensors are attached to the inner side of the garment to be in direct contact with the skin of the rescuer 104. In some implementations, the sensors can be attached to the active areas 302-322 through sensor carriers, which include a layer of high-traction or anti-slip material for contacting the skin of an individual such that the sensor remains undisturbed by movement of the rescuer during CPR treatment. In some implementations, the sensors themselves can include one or more anti-slip elements. The active areas 302-322 can include a foam or inflatable material for pressing the sensors firmly against the individual. Regardless of the particular implementation, the active areas 302-322 are integrated into the garment 300 to be worn by the rescuer 104 to enable physiological signals to be continuously measured in an extremely convenient, unobtrusive and effective way with little or no intervention needed on the part of the rescuer 104. The sensors can be connected by a cable 326 to one or more connectors 328 and 330. Connectors 328 and 330 can be connected wirelessly (e.g., bluetooth or WiFi connection) or through a cable 332 to a processor (e.g., a processor integrated in defibrillator 112).

In some implementations, the active areas 302-322 are configured to provide haptic feedback to the rescuer 104. For example, each of the active areas 302-322 can include a haptic substrate and a flexible surface. The haptic substrate can also be referred to as a haptic mechanism, a haptic layer, and/or a tactile element. The haptic substrate can be a surface-reconfigurable haptic element capable of changing its surface features in response to one or more activating signals. The haptic substrate can include multiple tactile or haptic regions that can be independently controlled and activated. Since each tactile region can be independently activated, a specific surface pattern of haptic substrate can be composed in response to the pattern activating signals. Each haptic region can be further divided into multiple haptic bits wherein each bit can be independently excited, activated, or deactivated.

The flexible surface layer can be made of soft and/or elastic materials such as silicone rubber, which is also known as polysiloxane, fabric, or other conformable material. The flexible surface layer can change its surface shape or texture in response to a physical pattern of the haptic substrate. In some implementations, the flexible surface layer can be a flexible touch sensitive surface, which is capable of accepting user inputs. The flexible touch sensitive surface can be divided into multiple regions wherein each region of the flexible touch sensitive surface can accept an input when the region is being touched or depressed (e.g., by bended elbows).

The flexible touch surface layer can include a mechanism for wireless power transfer between a processor (e.g., a processor integrated in defibrillator 112) and the flexible structure. It should be noted that the wireless power transfer may or may not be haptically enabled. The implementation of wireless power transfer, for example, may include one or more of inductive coupling, evanescent coupling, resonant induction, inductive charging, adaptive induction, electrical conduction, RF transfer or the like. The flexible touch surface layer can include a wireless circuitry for data transfer between a processor (e.g., a processor integrated in defibrillator 112) and the flexible structure.

The haptic substrate can include resonant mechanical elements, piezoelectric materials, micro-electro-mechanical systems ("MEMS") elements, thermal fluid pockets, MEMS pumps, variable porosity membranes, laminar flow modulation, and/or other elements that can produce a haptic signal (e.g., a haptic feedback to assist the rescuer 104 in performing CPR). The haptic substrate can include one or more actuators, which can be constructed from fibers (or nanotubes) of electroactive polymers ("EAP"), piezoelectric elements, fiber of shape memory alloys ("SMAs"), and the like. EAP can include electrostrictive polymers, dielectric elastomers, conducting polymers, ionic polymer metal composites, responsive gels, bucky gel actuators, or a combination of the above-mentioned EAP materials. SMA can include copper-zinc-aluminum, copper-aluminum-nickel, nickel-titanium alloys, or a combination of copper-zinc-aluminum, copper-aluminum-nickel, and/or nickel-titanium alloys. In some implementations multiple actuators (e.g., EAP, piezoelectric elements, and/or SMA) are combined to generate a particular haptic signal through a deforming mechanism.

The deforming mechanism can provide a pulling and/or pushing force to translate elements in the haptic substrate causing the flexible surface to deform. For example, when deforming mechanism creates a vacuum between the flexible surface and the haptic substrate, the flexible surface is pushed against haptic substrate causing the flexible surface to transfer a pattern of the haptic feedback to the rescuer 104.

The haptic feedback can be provided on particular areas of the body of the rescuer 104, to indicate a particular movement that is to be performed or adjusted. The haptic feedback can be provided as a vibration with different frequencies or as a continuous signal, as a vertical displacement, as a lateral displacement, and as a push or pull force. In some implementations, one or more characteristics of the haptic feedback (e.g., location, duration, variation type, frequency, amplitude and/or direction of displacement) are associated to a particular action and/or phase of the CPR treatment. For example, an increase/decrease in the frequency or amplitude of the haptic feedback can indicate to the rescuer 104 that an applied force should be similarly modified. As another example, active areas 310 and 312 can provide a haptic feedback (e.g., high frequency impulse) on the pectoral region of the rescuer 104 to indicate the rescuer 104 to push down. The duration of the haptic feedback (e.g., high frequency impulse) that is provided on the pectoral region of the rescuer 104 can indicate to the rescuer 104 an optimal time interval to push down. As another example, active areas 306 and 308 can provide a haptic feedback (e.g., low frequency impulse) on the trapezius muscle of the rescuer 104 to indicate the rescuer 104 to pull up. As another example, active areas 314 and 316 can provide a haptic feedback to the rescuer 104 to indicate the rescuer to straighten the elbows. As another example, active areas 302 and 304 can provide a haptic feedback (e.g., vertical displacement) to the rescuer 104 to indicate the rescuer to align the shoulders. In some implementations, the active areas 302-322 are configured to provide visual feedback in parallel with the haptic feedback provided to the rescuer 104. For example, the active areas 302-322 are capable of changing textile colors, which enables a second rescuer 106 and the camera 110 to simultaneously monitor the haptic feedback.

The garment 300 can include a plurality of markers 302a-322b that are configured to enhance an image detection of the rescuer position with the camera 110. Each region of interest of the rescuer body can include one or more markers. For example, shoulders include markers 302a-302c and 304a-304c, back includes markers 306a and 308a, pectorals include markers 310a, 310b, 312a, and 312b, elbows include markers 314a-c and 316a-b, wrists include markers 318a-b, 320a-b and 322a-b, and hips include markers 324a-b. In some implementations, one or more markers (e.g., markers 302a-302c, 304a-304c, 318a, 318b, 320a, and 320b) are attached to one or more active areas (e.g., active areas 302, 304, 306, 308, 310, 312, 318, and 320). One or more markers (e.g., markers 314a and 316a) can intersect one or more active areas (e.g., active areas 314 and 316). One or more markers (e.g., markers 314b and 316b) can be attached to the garment 300, outside of any active area (e.g., active areas 314 and 316).

The markers can be characterized by particular geometrical shapes (e.g., circles or rectangles) that can be automatically identified by an image processing algorithm. For example, the markers can be clustered in groups corresponding to different regions of the body of the rescuer 104. Each group of markers can have a particular geometrical shape that can be different from other groups, to enable a differentiation between a left and right side (e.g., 318a-318b and 320a-320b) or between one region and another (e.g., shoulders and elbows) of the rescuer 104.

The markers can be characterized by particular colors that provide an enhanced contrast relative to the background (e.g. color of the active areas and/or the color of the garment) that can be automatically identified by an image processing algorithm. The markers of a particular group, associated with a body region of the rescuer 104 can be arranged in a particular geometrical configuration (e.g., lines, triangles, circles or matrix). The geometrical configuration of the markers can be used to differentiate between a left and right side or between one region and another (e.g., shoulders and elbows) of the rescuer 104.

Figure 4A:
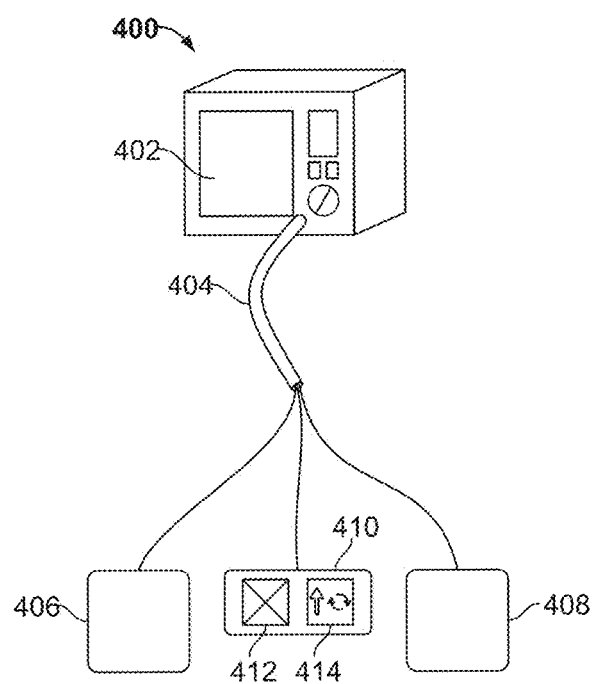
FIGS. 4A and 4B show a portable defibrillator and ancillary components arranged to provide feedback and instruction to rescuers in accordance with certain embodiments.

Referring to FIG. 4A, an example system 400 is shown in which a defibrillator 402, including a standard configuration, is upgraded to provide an additional user feedback functionality. The defibrillator 402 is connected to an electrode assembly by way of a wiring harness 404. The wiring harness 404 can include a number of wire leads that are connected together by a common plastic shroud that can surround the wires or can have been integrally formed around the wires such as through an extrusion process, and can be connected to the defibrillator 402 by way of a single plug. For example, the defibrillator 402 can be provided with a female or male connection, and the plug can be provided with a corresponding connection in a manner that is well known in the art. The wires can carry power from the defibrillator 402, such as current to provide a shock to a patient who is being provided with emergency care, or to the defibrillator 402, such as in the form of signals for generating ECG information, accelerometer information, and measurements of trans-thoracic impedance of a patient.

The electrode assembly in this example includes a first electrode 406, a second electrode 408, and a chest compression assembly 410. The first electrode 406 can be configured to be placed above the patient's right breast, while the second electrode 408 can be configured to be placed below the patient's left breast. During a rescue operation, printed insignia on one or both of the electrodes 406, 408 can indicate to a rescuer how to deploy the electrodes 406, 408, and where each of them should be placed. In addition, the defibrillator 402 can display such instructions on a graphical display and can also provide verbal instructions to supplement was is shown in the visual instructions, such as instructions for the sequential operation of the defibrillator.

The chest compression assembly 410, in this example, includes a detector 412 and a display 414. The detector 412 can include a plastic housing within which is mounted an accelerator assembly. The accelerator assembly can move with the housing as chest compressions are performed on a patient so that motion of the accelerometer matches motion of the patient's sternum. The detector 412 is shown in the figure as having an "X" printed on its top surface to indicate to the rescuer where to place his or her hands when delivering chest compressions to a patient. The accelerator in the housing can be connected to pass signals through harness 404 to defibrillator 402 (or can include a wireless transceiver for passing the information wirelessly), which can be provided with circuitry and or software for converting such signals into the indications about the rate and depth of compressions being performed on the patient, in manners such as those described below.

The display 414 can provide feedback that is directed to the rescuer who is performing chest compressions. In this example, the feedback comprises symbols similar to those shown on the display of defibrillator 112 in FIGS. 1A-1D, in particular, a real-time representation of the rescuer who performs chest compressions synchronously displayed with an optimized rescuer position. The representation can be selected to be independent of the orientation from which it is viewed, so that it has the same meaning to a rescuer who is on the right side of the patient as to a rescuer who is on the left side of the patient. In that manner, the system 400 does not need to determine where the rescuer is positioned. Also, a haptic vibrating mechanism can be provided at the assembly 410, so as to provide tactile beats or metronomes for a user to follow in providing chest compressions.

Figure 4B:
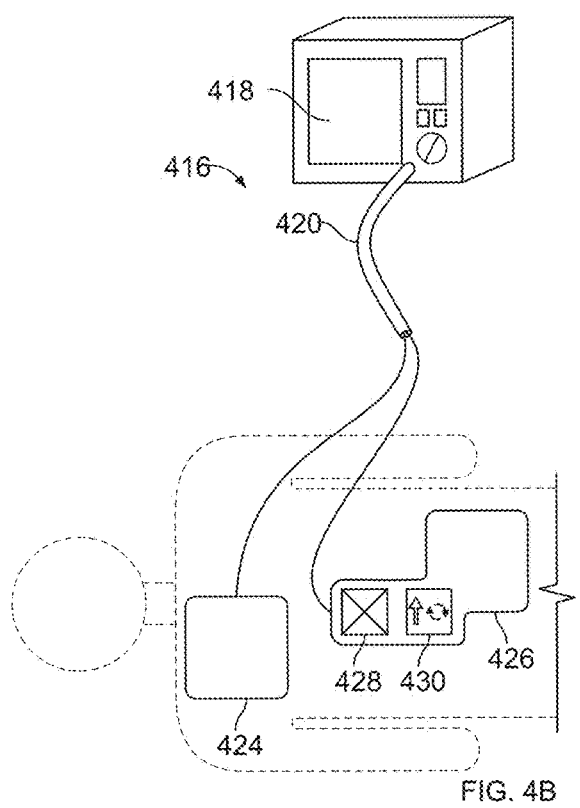

FIG. 4B shows a slightly different arrangement in a system 416 that includes a defibrillator 418 that is the same as defibrillator 402. In actual implementation also, the same defibrillator could be used with two different types of electrode assemblies like those shown in FIGS. 4A and 4B. With specific reference to FIG. 4B, a wiring harness 420 in this example can be the same as wiring harness 404 in FIG. 4A, though here it connects defibrillator 418 to an electrode 424, and an assembly 426. The electrode 424 can simply be a single electrode that is connected to receive energy from the defibrillator 418, and is arranged to be placed in a conventional manner above a patient's right breast. The electrode 424 can also include mechanisms for sensing an ECG reading from a patient, and for communicating sensed parameters back to the defibrillator 418.

The assembly 426 can take a slightly L-shaped form, with one leg comprising an electrode designed to be placed below a patient's left breast, and another leg arranged to lie in a line with the patient's sternum. The assembly can be mounted on a flexible foam later that includes a gel layer on the bottom of the electrode for conducting a shocking pulse to a patient, but no gel under the sensor portion. However, the sensor portion can have a form of adhesive on its bottom side so that the accelerometer does not bounced and separate from the patient during chest compressions, and thus give an inaccurate reading to the defibrillator 418.

In this example, the hypothetical patient is shown in dotted lines to indicate how the electrode 424 and the assembly 426 can be positioned in actual use. Before they are deployed, however, the various electrodes and assemblies can be stored in a sealed packet, and the wires can be coiled to reduce needed space, in conventional manners. At the time of an emergency, the wires can have already been plugged into the defibrillator (e.g., via the wires extending through a sealed hole out of a packet in which the electrodes are stored to keep their gels moist). A rescuer can then open the package, plug the wires in if they are not already plugged in, and if necessary, read instructions on the back sides of the electrodes regarding the proper manner to apply the electrodes—e.g., with graphics that show the peeling off of covers over the electrode gels and also show images of the proper placement of the electrodes on a line-drawn patient.

In additional to electrodes, the assembly 426 can include a sensor assembly 428 and a display 430, similar to the sensor assembly 412 and display 414 in FIG. 4A. In addition, the components that provide functionality of the assembly 428 and display 430 can be the same as those described above for assembly 412 and display 414 in FIG. 4A. In this example, though, the assembly 428 and display 430 are connected directly to the electrode 426 by flexible structures that are arranged and sized so as to place the electrode and sensors in appropriate locations for a patient (under a left breast and aligned over the top of the sternum). Such an arrangement allows the system 416 to have fewer components that need to be applied to a patient then the system 400, while still having the flexibility to space the two electrodes relative to each other depending on the size of the patient—e.g., because the electrodes are separate from each other, it can be easier to position them both on small patients and very tall/long patients.

In both of the systems 400, 416, the placement of a display near the hands of a rescuer can provide one of more benefits in some implementations. For example, a rescuer is typically looking at his or her hands when applying chest compressions, both because it is most natural to look forward, and as a mechanism to obtain feedback on how deep the chest compressions are and how the patient is doing. Thus, the rescuer can see the feedback without having to look around, and can constantly receive the feedback even while performing chest compressions. Also, the components can be provided in such locations conveniently and with relatively low cost, since the electrodes and accelerometers will already be provided, and a display need simply be added to one of these existing components (though in other implementations, the display can be located elsewhere). The feedback device also is naturally positioned to provide haptic feedback, which might be more directly processed by a rescuer. And by using visual feedback that is in the field of view of a particular rescuer and using haptic feedback, the system can reduce "attention pollution" at a scene, in that is lessens the level of noise and other distractions that other rescuers have to deal with in a very stressful environment.

Feedback devices away from the main medical device can also take other forms. For example, an LED can be provided in the top surface of one of the electrodes or near a puck, and the LED can blink to indicate a rate of chest compressions to be performed, and stay solid on to indicate that rescuers should switch positions. Also, an LED or graphical display can be provided on the ventilation bag 412, such as to blink to indicate a rate at which the bag is to be squeezed, and can be made solid in coordination with a display for the person performing chest compressions being made solid. In other words, the same signal can be provided to each of the rescuers to switch places, though on the respective subsystem that they are currently operating. As a result, the rescuers will only need to know a single "change" signal and will be able to react more intuitively and more quickly.

Figure 4C:
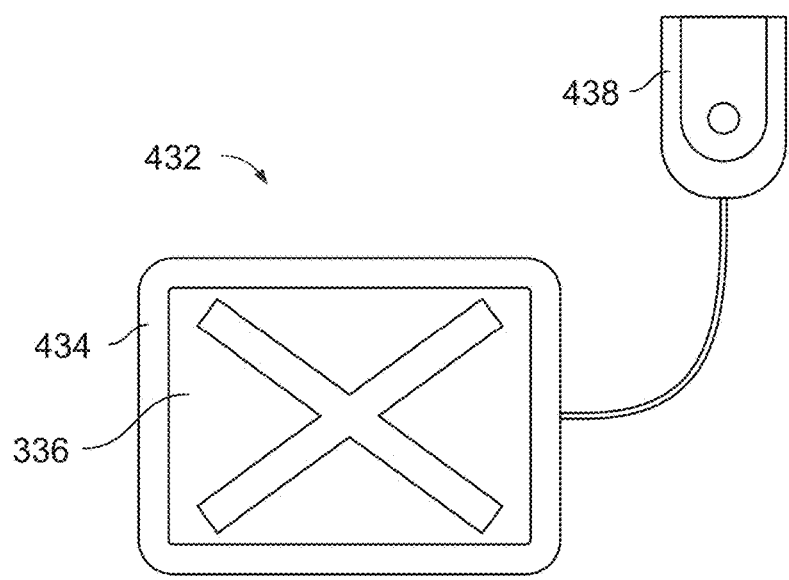
FIGS. 4C-4E show chest compression pucks that can capture information provide from activities of a rescuer in accordance with certain embodiments.
Figure 4D:
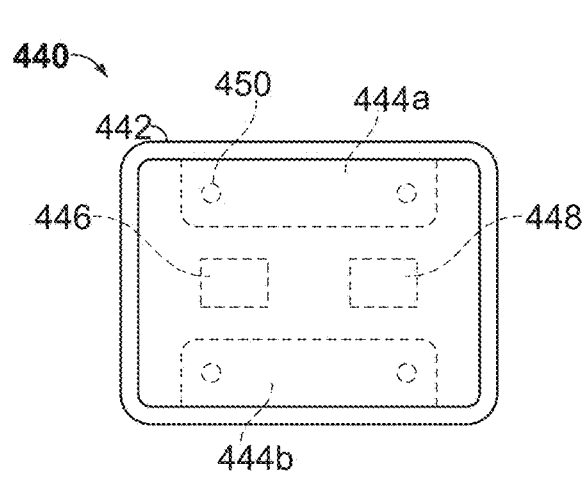
Figure 4E:
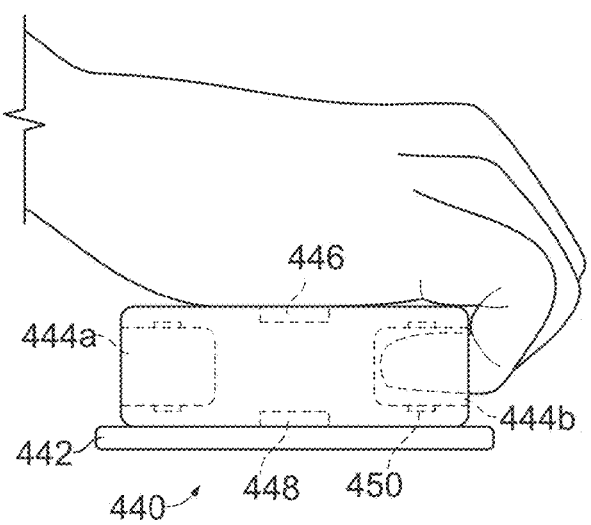

FIGS. 4C-4E show chest compression pucks that can capture information from a rescuer. In general, typical pulse oximetry sensor components can be integrated into a device on or in which a rescuer places his or her fingers, and can be used to provide a connected (wired or wirelessly) medical device such as a defibrillator, with indications of the blood oxygen level and pulse rate of a rescuer holding the device, which in these examples can be referred to as a CPR puck. The pucks shown in FIGS. 4C-4E can be provided as part of the systems also shown in FIGS. 4A and 4B, such as by integrating the components for sensing rescuer condition into the components in those other figures.

Referring now specifically to FIG. 4C, there is shown an assembly 432 made up of a puck housing 336 and substrate 434. The substrate 434 can have on its lower side a gel-based adhesive so that the assembly 432 adheres to the chest of a patient on which it is placed. The housing 336 can in turn be solidly adhere to the top of the substrate 434 do that the housing 336 moves with a patient's sternum when a rescuer places his or her hands on top of the "X" shown on the top surface of the housing 436 and performs chest compressions. Connected to the substrate 434 and/or housing 336 by wire is a pulse oximeter 438. The pulse oximeter can report a blood oxygen level and pulse rate through the wire from which hit is attached into the remainder of the assembly 432, from which it can be reported to a defibrillator or other medical device, either wirelessly or by wired connection.

In operation, when a rescuer begins performing chest compressions, he or she can be instructed to slip a fingertip into the pulse oximeter 438 before placing his or her palms on top of the housing 336. The wire can permit movement of the rescuer's fingertip as they perform chest compressions, while measuring the relevant values. Such values can then be used, as discussed above, along with other factors such as rate and depth of compressions, to determine when the rescuer should be instructed to stop performing chest compressions and yield to another rescuer. Also, the assembly 432 can be provided as a stand-alone unit separate from a defibrillator or other medical, so as to provide more general feedback to a rescuer, where the feedback integrates consideration of rescuer blood oxygen level, pulse, or both.

Referring to FIGS. 4D and 4E, there is shown a top and side section view of an assembly 440 that is similar to assembly 432 in FIG. 4C, but integrates sensing functionality for the rescuer into the puck housing.

Again, the housing is shown on top of an adhesive substrate 242, but in this example, the housing is provided with depressions 244a, 244b into which a rescuer can slide his or her fingertips while performing chest compressions, as shown by the hand in FIG. 4E. The housing is provided with depressions 244a, 244b on opposed sides, so that rescuers on both sides of a patient can use the assembly 440 and take advantage of its rescuer monitoring functionality. Also, as shown, sensors 250 can be provided at multiple locations, including four different locations to reflect rescuers who can be on either side of the patient and can places fingers from their right or left hands into the depressions 244a, 244b.

The assembly can simply send signals back to a medical device such as a defibrillator. Separately, the assembly 440 can modify or analyze the signals right on the assembly 240 in the housing. Thus, for example, an oximeter processor 248 is shown inside the housing and can receive signals from the sensors 250 and convert them partially or fully into blood oxygen and pulse rate values that can then be displayed or further processed on the assembly 440 (e.g., to identify that the rescuer is becoming fatigued). Similarly, an accelerometer pack 246 can be provided inside the housing in a position so as to sense proper motion of the patient's sternum. The pack 246 can, for example, compute depths of compressions and rates of compressions, and can also be connected to an output mechanism on the assembly 440 or connected to a medical device that is separate from the assembly 440 so as to provide chest compression feedback in manners like those discussed above and below.

Figure 5:
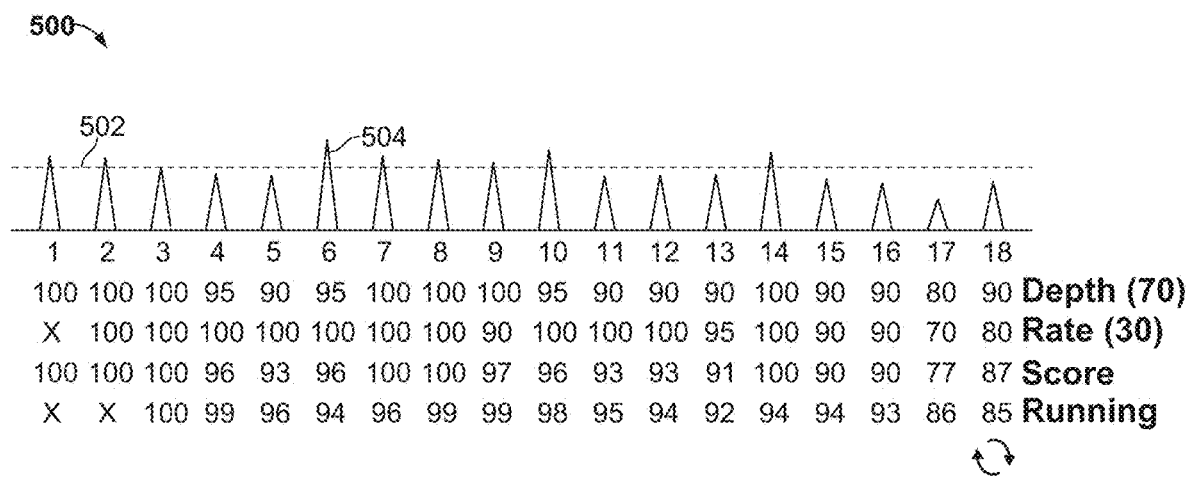
FIG. 5 shows example chest compression inputs and mechanisms for analyzing the inputs to determine whether a different person should provide chest compressions.

FIG. 5 shows example chest compression inputs and mechanisms for analyzing the inputs to determine whether a different rescuer should provide chest compressions. In general, the illustrated example includes a series of eighteen chest compressions 500 that have been graphed along a horizontal time axis, along with a variety of numbers that represent parameters of how the chest compressions were performed. Such sensed compression data and derived numbers can then be used to determine when the quality of the chest compressions indicates that the rescuer is getting fatigued and cannot maintain the optimized CPR technique identified by the system, and the system should indicate to the rescuer that they should switch with another, fresher rescuer.

Referring more specifically to the graphed compressions, a dashed line 502 represents a target chest compression depth. Each of the spikes 504 indicate a distance level of downward compression (y axis), graphed according to time (x axis). In particular, the compressions are sharp motions followed by pauses, with the overall pattern repeated eighteen times during the time (which can be a fraction of a minute when the rescuer is performing about 100 compressions per minute). Such compressions can be sensed by an accelerometer assembly that is between the hands of the rescuer performing chest compressions and the sternum of the patient. Sensed signals can then be passed through a wiring harness to circuitry and software in a defibrillator or other medical device that can analyze the signals to identified compression depths and timing of the chest compressions.

As can be seen, the initial chest compressions are at an appropriate level and an appropriate rate, but began to dip at the fourth and fifth compressions. The compressions then pick up and hit the dashed line 502, perhaps because the fall in compressions caused a defibrillator to indicate to a rescuer that they should compress harder, and the user followed such direction. The depth of compressions over time then falls again at compressions 11, 12 and 13, but then picks up at 14 and falls yet again near the end, indicating that the user has become fatigued.

Below the graph are shown numbers that, for this example, indicate values that can be computed by a defibrillator that is connected to a system for determining when to signal that a provider of chest compressions to a patient should be changed by the system. The top row shows a score that can be given to a user to rate the quality of the depth of the chest compressions. Such a score can be given a baseline of 100 around a depth that approximates the desired line of 502. The score can fall the further one gets from line 502, though the score can fall more quickly for deviations on the under-compression side than the over-compression side, e.g., if a determination is made that under-compression is a more serious error than over-compression. Thus, for example, the fifth compression falls below line 502 by an amount less than the sixth compression falls above the line, but the fifth compression receives a lower score than does the sixth compression.

In this example, the depth of compression factor is provided 70% of a weighting in determining an overall score for the quality of the chest compression. The other 50% of the score is driven by the rate at which the user provides the compressions. Thus, for example, one can see fairly even spacing for compressions two through eight, but a slight delay for compression nine, so that the ninth compression receives a score of 90 instead of a score of 100. In addition, one can see lengthening delays between compressions at the end of the period. The rate scores reflect, in each instance, how far a compression was performed from the time at which it was supposed to be performed according to protocol. Again, the scores are scaled to a maximum of 100 for ease of explanation, but could take other forms also.

The third line in the numbers indicates an overall score for each of the compressions, where the overall score is simply the combined weighted value of the two component scores for depth and rate, respectively. Finally, the fourth line shows a running score that is a running average of the current score and the two previous scores. By using a running average, singular deviations from a perfect compression can be ignored, while lingering deviations can be captured so that continual failure by a user, which indicates fatigue of the user, can result in the generation of a signal to switch users in performing chest compressions. Thus, for example, compression number five is a bad compression, but the running score is relatively high because the previous two compressions were better.

In this example, the trigger for generating an indication that users should change position is a running score at or below 85. Thus, although the running score in the example rises and falls as a user has periodic problems with performing compressions, it does not fall to the triggering level until compression eighteen, after there had been three weak compressions in a row that were also spaced too far apart—so that the running average score really fell. In actual implementation, software can monitor the value as a user provides compressions, can periodically update the value (e.g., once for each compression or on another basis), and can cause a defibrillator, such as defibrillator 112, to emit output to one or more rescuers to indicate the need for a change, such as the indication shown in the prior figures above.

While the particular running average scoring technique described is provided for its simplicity and ease of understanding, different approaches can be used to identify when a user is likely becoming too fatigued to maintain quality chest compressions or other components of CPR. For example, various inputs can be subjected to derivations in order to determine rates of change of those inputs. An indication to change rescuers can be generated when the rate of change in the quality of performance exceeds a preset amount in a negative direction. Also, models can be generated to represent fatigued users, and actual inputs can be compared to such models to indicate when fatigue is setting in for a real user and to cause an alert to be generated.

In some instances, such as when the number of rescuers is known, data can be stored across multiple cycles of chest compression sessions for each of the users. For example, the system can identify in early cycles of a rescue that one of the rescuers has a sudden drop-off in chest compression performance but then recovers, and can store such understanding and use it in subsequent cycles so as to not trigger an indication to change rescuers simply because the particular rescuer is having momentary problems. Another rescuer can be seen to have a slower drop in performance but can be more erratic in his provision of chest compressions, so that a system can permit more variability before it triggers an indication to switch rescuers, since variability by that user can not indicate fatigue, but can simply be standard variability in the manner in which the user performs chest compressions. Other factors can also be taken into account in addition to depth and rate of providing chest compressions. For example, a heart rate monitor can be applied to a rescuer and an increase in heart rate can indicate fatigue by the rescuer, and can be used to generate a signal to switch rescuers. Also, the shape of a compression profile can be used, such that a jerky or sharp profile can indicate fatigue by a user, and also contribute to the triggering of a signal to switch rescuers.

Figure 6A:
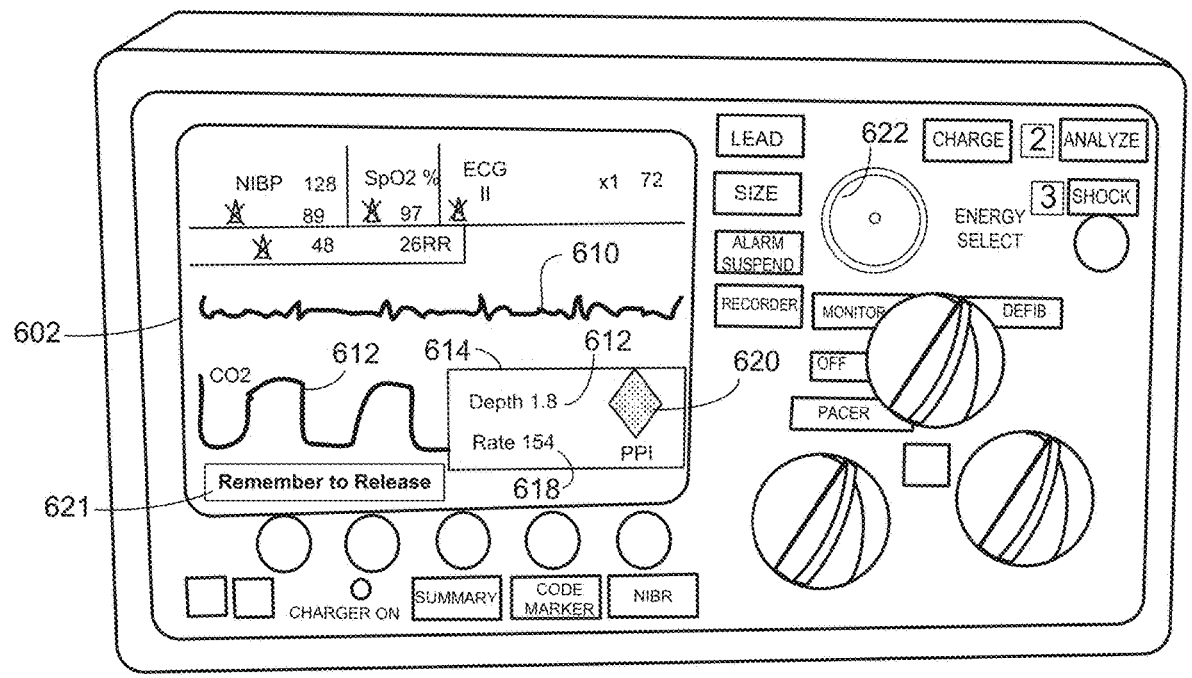
FIGS. 6A and 6B illustrate a defibrillator showing some types of information that can be displayed to a rescuer.
Figure 6B:
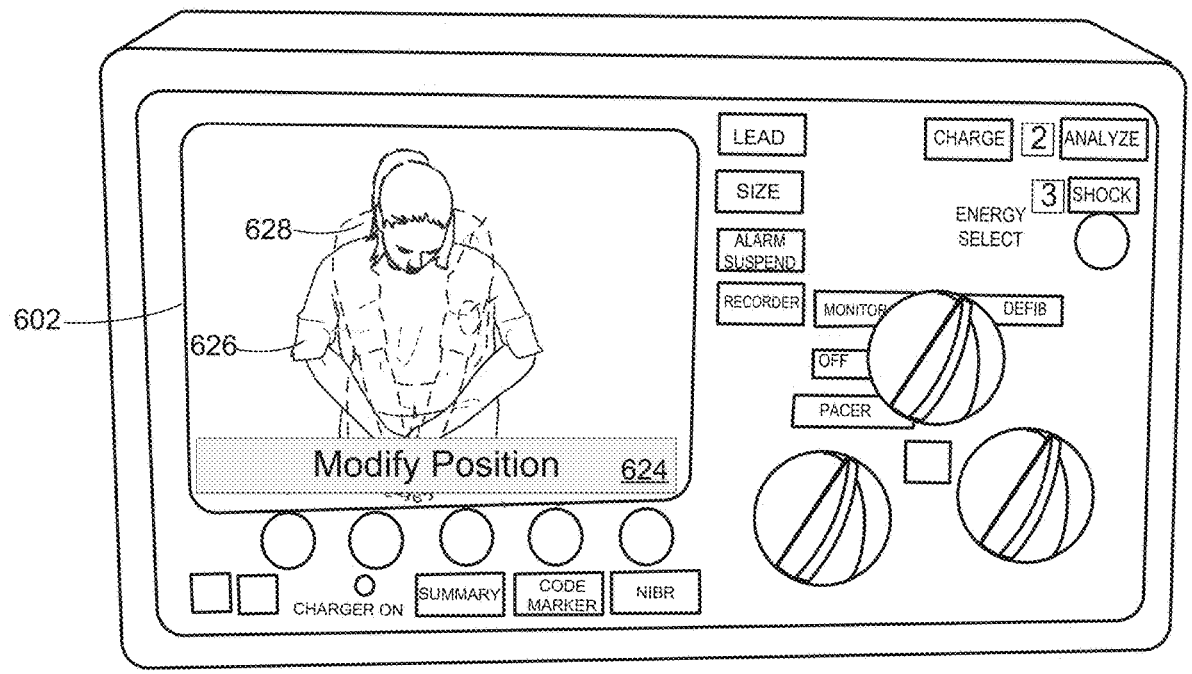

As illustrated in FIGS. 6A and 6B, a defibrillator or a computing device including a display of can provide real-time feedback to the rescuers. For illustrative purposes, two particular examples of feedback are shown on a display 602 of the defibrillator 112. FIG. 6A shows a defibrillator showing some types of information that can be displayed to a rescuer. In the figure, a defibrillation device 600 with a display portion 602 provides information about patient status and CPR administration quality during the use of the defibrillator device. As shown on display 602, during the administration of chest compressions, the device 600 displays information about the chest compressions in box 614 on the same display as is displayed a filtered ECG waveform 610 and a CO2 waveform 612 (alternatively, an SpO2 waveform can be displayed).

During chest compressions, the ECG waveform is generated by gathering ECG data points and accelerometer readings, and filtering the motion—induced (e.g., CPR-induced) noise out of the ECG waveform. Measurement of velocity or acceleration of chest compression during chest compressions can be performed according to the techniques taught by U.S. Pat. No. 7,220,335, titled Method and Apparatus for Enhancement of Chest Compressions During Chest Compressions, the contents of which are hereby incorporated by reference in their entirety. Displaying the filtered ECG waveform helps a rescuer reduce interruptions in CPR because the displayed waveform is easier for the rescuer to decipher. If the ECG waveform is not filtered, artifacts from manual chest compressions can make it difficult to discern the presence of an organized heart rhythm unless compressions are halted. Filtering out these artifacts can allow rescuers to view the underlying rhythm without stopping chest compressions.

The CPR information in box 614 is automatically displayed when compressions are detected by a defibrillator. The information about the chest compressions that is displayed in box 614 includes rate 618 (e.g., number of compressions per minute) and depth 616 (e.g., depth of compressions in inches or millimeters). The rate and depth of compressions can be determined by analyzing accelerometer readings. Displaying the actual rate and depth data (in addition to, or instead of, an indication of whether the values are within or outside of an acceptable range) can also provide useful feedback to the rescuer. For example, if an acceptable range for chest compression depth is 1.5 to 2 inches, providing the rescuer with an indication that his/her compressions are only 0.5 inches can allow the rescuer to determine how to correctly modify his/her administration of the chest compressions (e.g., he or she can know how much to increase effort, and not merely that effort should be increased some unknown amount).

The information about the chest compressions that is displayed in box 614 also includes a perfusion performance indicator (PPI) 620. The PPI 620 is a shape (e.g., a diamond) with the amount of fill that is in the shape differing over time to provide feedback about both the rate and depth of the compressions. When CPR is being performed adequately, for example, at a rate of about 100 compressions per minute (CPM) with the depth of each compression greater than 1.5 inches, the entire indicator will be filled. As the rate and/or depth decreases below acceptable limits, the amount of fill lessens. The PPI 620 provides a visual indication of the quality of the CPR such that the rescuer can aim to keep the PPI 620 completely filled.

As shown in display 602, the filtered ECG waveform 610 is a full-length waveform that fills the entire span of the display device, while the second waveform (e.g., the CO2 waveform 612) is a partial-length waveform and fills only a portion of the display. A portion of the display beside the second waveform provides the CPR information in box 614. For example, the display splits the horizontal area for the second waveform in half, displaying waveform 612 on left, and CPR information on the right in box 614.

The data displayed to the rescuer can change based on the actions of the rescuer. For example, the data displayed can change based on whether the rescuer is currently administering CPR chest compressions to the patient. Additionally, the ECG data displayed to the user can change based on the detection of CPR chest compressions. For example, an adaptive filter can automatically turn ON or OFF based on detection of whether CPR is currently being performed. When the filter is on (during chest compressions), the filtered ECG data is displayed and when the filter is off (during periods when chest compressions are not being administered), unfiltered ECG data is displayed. An indication of whether the filtered or unfiltered ECG data is displayed can be included with the waveform.

Also shown on the display is a reminder 621 regarding "release" in performing chest compression. Specifically, a fatigued rescuer can begin leaning forward on the chest of a patient and not release pressure on the sternum of the patient at the top of each compression. This can reduce the perfusion and circulation accomplished by the chest compressions. The reminder 621 can be displayed when the system recognizes that release is not being achieved (e.g., signals from an accelerometer show an "end" to the compression cycle that is flat and thus indicates that the rescuer is staying on the sternum to an unnecessary degree). Such a reminder can be coordinated with other feedback as well, and can be presented in an appropriate manner to get the rescuer's attention. The visual indication can be accompanied by additional visual feedback near the rescuer's hands, and by a spoken or tonal audible feedback, including a sound that differs sufficiently from other audible feedback so that the rescuer will understand that release (or more specifically, lack of release) is the target of the feedback. For example, the defibrillator 112 can emit a sound through speaker 622 in the form of a metronome to guide the rescuer 104 in the proper rate of applying CPR.

FIG. 6B shows the same defibrillator, but with a real-time feedback on optimizing the position, orientation and/or motion of the rescuer. In this example, an alert box 624 is shown across the bottom half of the display. The display 602 illustrates a current position 626 of the rescuer 104 overlapped by a template position 628 of the rescuer 104. The overlapping positions of the rescuer 104 are included in the display 602 to provide feedback to assist the rescuer 104 in improving the quality of the administration of chest compressions.

As described in more detail with reference to FIG. 10, the template position 628 of the rescuer 104 can be determined by a processor integrated in the defibrillator 112. The template position 628 can be determined based on the profile of the rescuer 104 and other parameters including past compression parameters (e.g., rate over several compressions and depth) and monitoring the rescuer directly (e.g., by determining a pulse and blood oxygen level of a rescuer). Such an analysis can recognize that rescuers tire progressively over time as they are providing chest compressions. For example, the depth of chest compressions can present a decreasing trend over time, and the rate of chest compressions present a tendency to become erratic or already became more erratic over time.

In some implementations, the template position 628 is continuously displayed by the defibrillator 112. In some implementations, the template position 628 is only displayed if the current position 626 of the rescuer 104 is significantly different from the template position 628. For example, if the elbows define an angle smaller than 160°, or the shoulders seem to form an angle larger than 5° with an intersecting horizontal axis, the display 602 displays the template position 628 overlapping the current position 626 of the rescuer 104. In some implementations, a color can be associated with the display of the current position 626 of the rescuer 104. For example, if the current position 626 of the rescuer 104 is determined to match the template position 628, the current position 626 can be displayed in green. If the current position 626 of the rescuer 104 is determined to be insignificantly different from the template position 628, the current position 626 can be displayed in yellow. If the current position 626 of the rescuer 104 is determined to be significantly different from the template position 628, the current position 626 can be displayed in red. In some implementations, a significant difference between the template position 628 and the current position 626 can also be visually represented by additional indicators, such as a blinking of the display on defibrillator 112. In addition, or as an alternative output mechanism that is designed to avoid distracting rescuer 106, haptic feedback can be provided to rescuer 104 through garment 300, described with reference to FIGS. 3A and 3B. Additionally, a puck or other item on which the rescuer 104 places her hands can be provided with mechanisms for vibrating the puck similar to mechanisms provided for vibrating portable communication devices (e.g., when an incoming telephone call is received on a smartphone). Such vibrating can be provided so as to minimize the amount of information that can distract other rescuers in the area, and can also more directly be used by the rescuer 104 to synchronize her chest compression activities with the output. For example, the vibrations can be periodic (approximate 100 times per minute) at the rate of performing chest compressions when the rescuer 104 should be performing compressions and can stop or be vibrated constantly when the rescuer 104 is to correct the position during CPR performance.

With feedback provided at the rescuer's hands, and because the rescuer 104 is providing the chest compressions directly with the hands, input by the system into the hands can be more directly applied with respect to the rescuer 104 keeping an appropriate pace. Such haptic feedback can also relieve the rescuer 104 of having to turn the head to view the display on defibrillator 112. Thus, a first type of feedback, such as pulsed visual, audible, or tactile feedback can be provided to guide a user in performing CPR, and that type of feedback can be interrupted and replaced with a different type of feedback such as constant sound or vibration to indicate that a rescuer is to correct a particular component of CPR (e.g., body position).

Figure 7A:
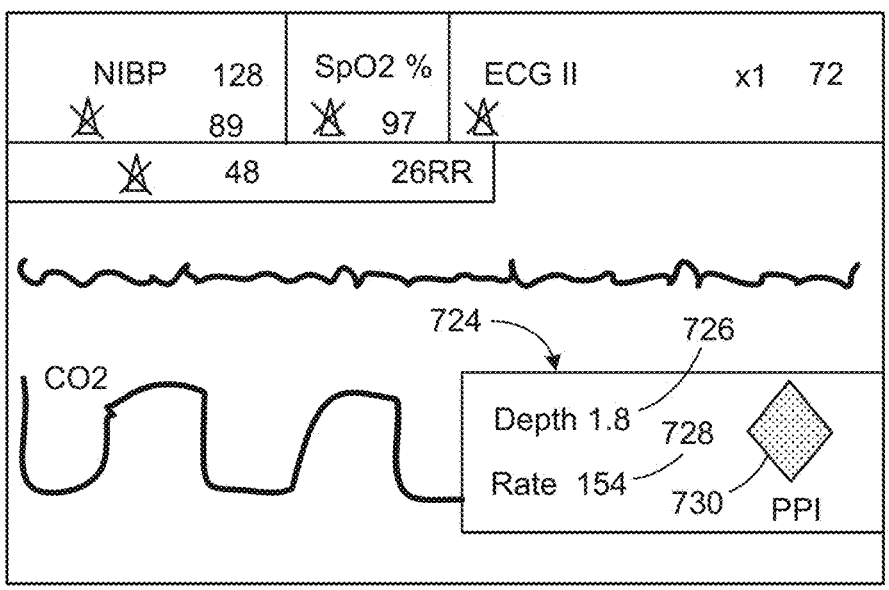
FIGS. 7A-7C show screenshots of a defibrillator display that provides feedback concerning chest compressions performed on a patient.
Figure 7B:
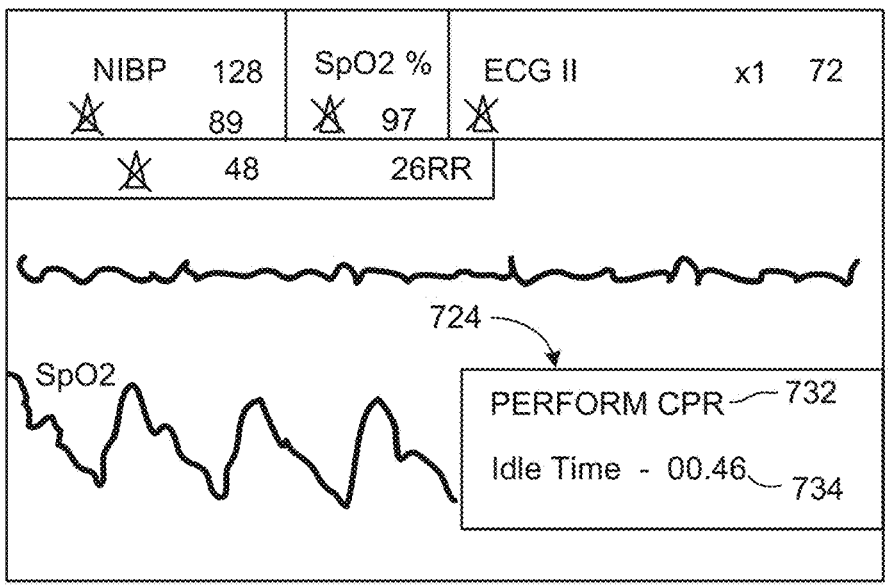
Figure 7C:
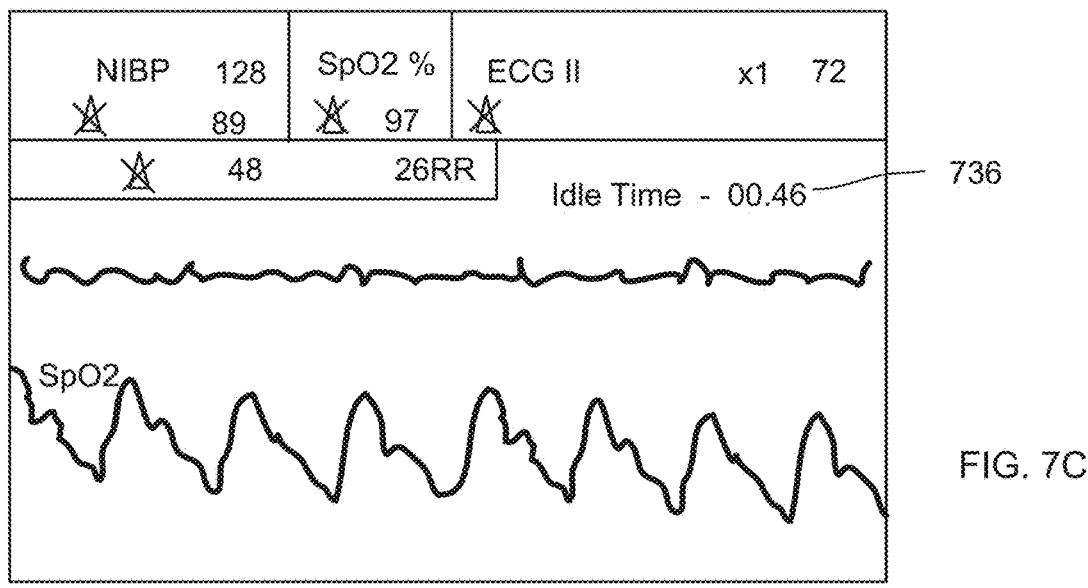

FIGS. 7A-7C show example screens that can be displayed to a rescuer on a defibrillator. Each of the displays can be supplemented with a display like box 602 in FIGS. 6A and 6B when the defibrillator determines that rescuers providing some component of care (e.g., chest compressions) should be changed.

FIG. 7A shows exemplary information displayed during the administration of CPR chest compressions, while FIGS. 7B and 7C show exemplary information displayed when CPR chest compressions are not being sensed by the defibrillator. The defibrillator automatically switches the information presented based on whether chest compressions are detected. An exemplary modification of the information presented on the display can include automatically switching one or more waveforms that the defibrillator displays. In one example, the type of measurement displayed can be modified based on the presence or absence of chest compressions. For example, $CO_2$ or depth of chest compressions can be displayed (e.g., a $CO_2$ waveform 720 is displayed in FIG. 7A) during CPR administration, and upon detection of the cessation of chest compressions, the waveform can be switched to display a $SpO_2$ or pulse waveform (e.g., a $SpO_2$ waveform 722 is displayed in FIG. 7B).

Another exemplary modification of the information presented on the display can include automatically adding/removing the CPR information from the display upon detection of the presence or absence of chest compressions. As shown in FIG. 7A, when chest compressions are detected, a portion 724 of the display includes information about the CPR such as depth 726, rate 728, and PPI 730. As shown in FIG. 7B, when CPR is halted and the system detects the absence of CPR chest compressions, the defibrillator changes the CPR information in the portion 724 of the display, to include an indication 732 that the rescuer should resume CPR, and an indication 734 of the idle time since chest compressions were last detected. In a similar manner, when the defibrillator determines that rescuers should change, the label 732 can change to a message such as "Change Who is Administering CPR." In some implementations, as shown in FIG. 7C, when CPR is halted, the defibrillation device can remove the portion of the display 724 previously showing CPR data and can display a full view of the second waveform. Additionally, information about the idle time 736 can be presented on another portion of the display.

Figure 8A:
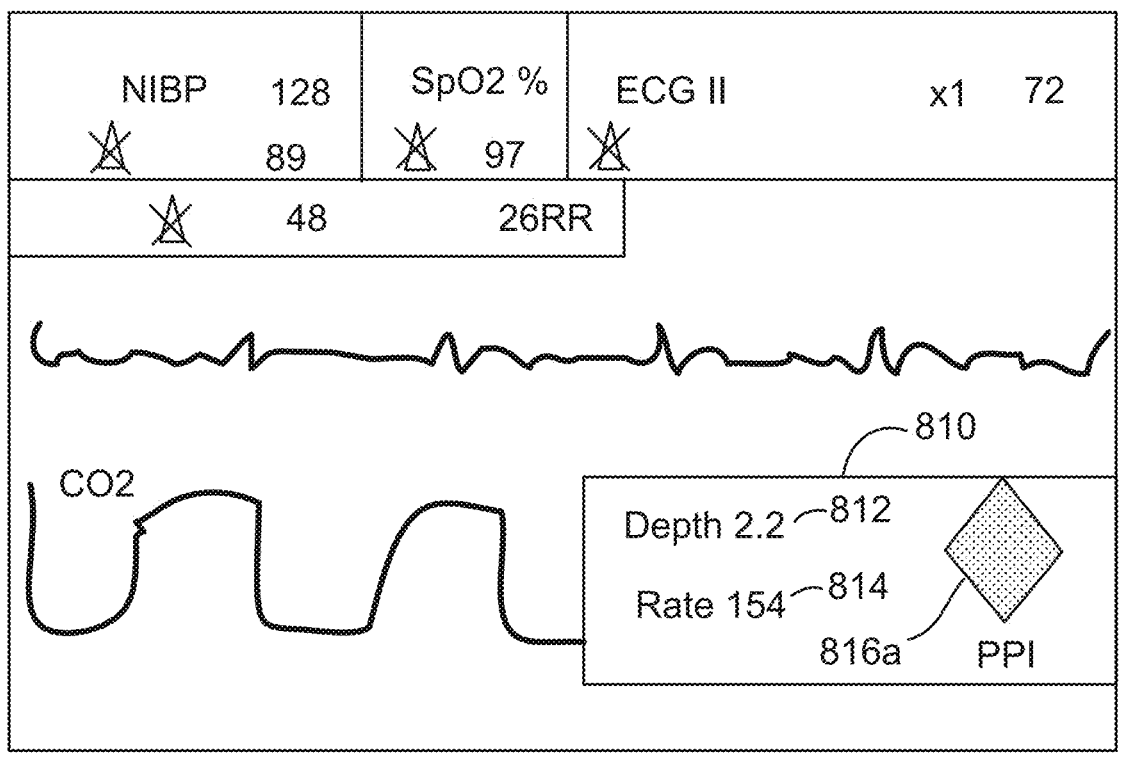
FIGS. 8A and 8B show screenshots providing feedback regarding a perfusion index created form chest compressions.
Figure 8B:
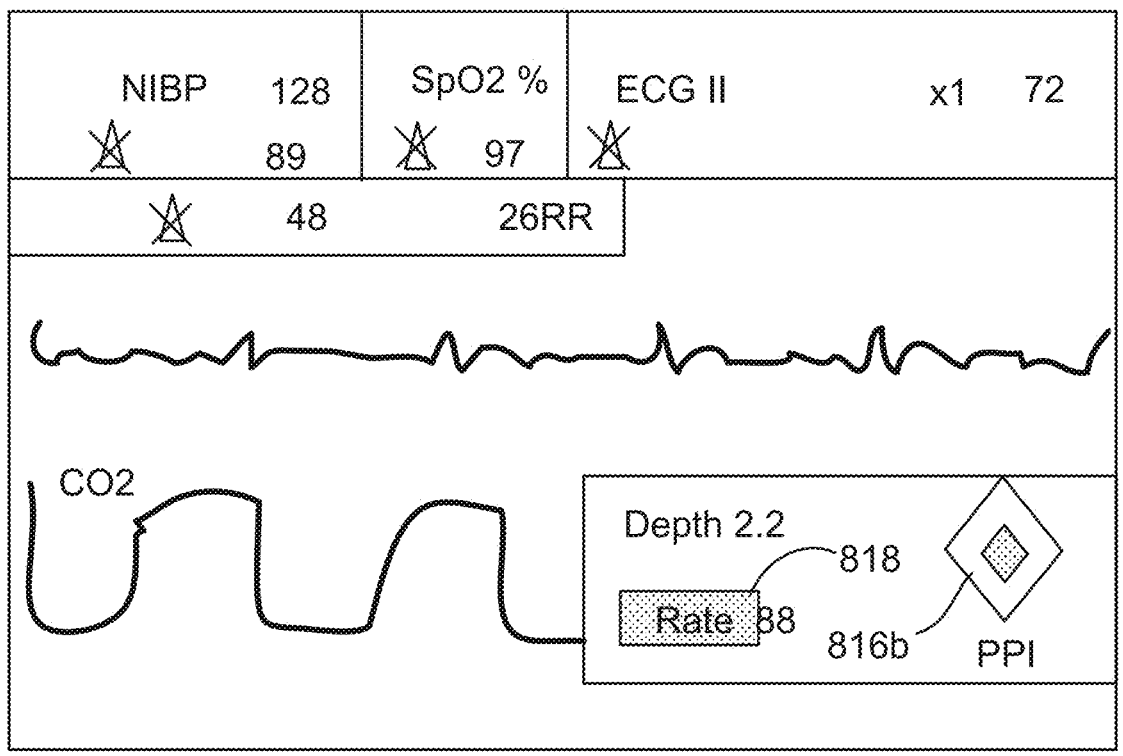

FIGS. 8A and 8B show defibrillator displays that indicate to a rescuer levels of perfusion being obtained by chest compressions that the rescuer is performing. FIG. 8A shows exemplary data displayed during the administration of CPR chest compressions when the CPR quality is within acceptable ranges, while FIG. 8B shows modifications to the display when the CPR quality is outside of the acceptable range.

In the example shown in FIG. 8B, the rate of chest compressions has dropped from 154 compressions per minute (FIG. 8A) to 88 compressions per minute. The defibrillator device determines that the compression rate of 88 compressions per minute is below the acceptable range of greater than 100 compressions per minute. In order to alert the user that the compression rate has fallen below the acceptable range, the defibrillator device provides a visual indication 818 to emphasize the rate information. In this example, the visual indication 818 is a highlighting of the rate information. Similar visual indications can be provided based on depth measurements when the depth of the compressions is shallower or deeper than an acceptable range of depths. Also, when the change in rate or depth indicates that a rescuer is becoming fatigued, the system can display a message to switch who is performing the chest compressions, and can also emit aural or haptic feedback to the same effect.

In the examples shown in FIGS. 8A and 8B, a perfusion performance indicator (PPI) 816 provides additional information about the quality of chest compressions during CPR. The PPI 816 includes a shape (e.g., a diamond) with the amount of fill in the shape differing based on the measured rate and depth of the compressions. In FIG. 8A, the depth and rate fall within the acceptable ranges (e.g., at least 100 compressions/minute (CPM) and the depth of each compression is greater than 1.5 inches) so the PPI indicator 816a shows a fully filled shape. In contrast, in FIG. 8B, when the rate has fallen below the acceptable range, the amount of fill in the indicator 816b is lessened such that only a portion of the indicator is filled. The partially filled PPI 816b provides a visual indication of the quality of the CPR is below an acceptable range.

As noted above with respect to FIG. 6A, in addition to measuring information about the rate and depth of CPR chest compressions, in some implementations the defibrillator provides information about whether the rescuer is fully releasing his/her hands at the end of a chest compression. For example, as a rescuer tires, the rescuer can begin leaning on the patient between chest compressions such that the chest cavity is not able to fully expand at the end of a compression. If the rescuer does not fully release between chest compressions the quality of the CPR can diminish. As such, providing a visual or audio indication to the user when the user does not fully release can be beneficial. In addition, such factors can be included in a determination of whether the rescuer's performance has deteriorated to a level that the rescuer should be instructed to permit someone else perform the chest compressions, and such information can be conveyed in the various manners discussed above.

Figure 9A:
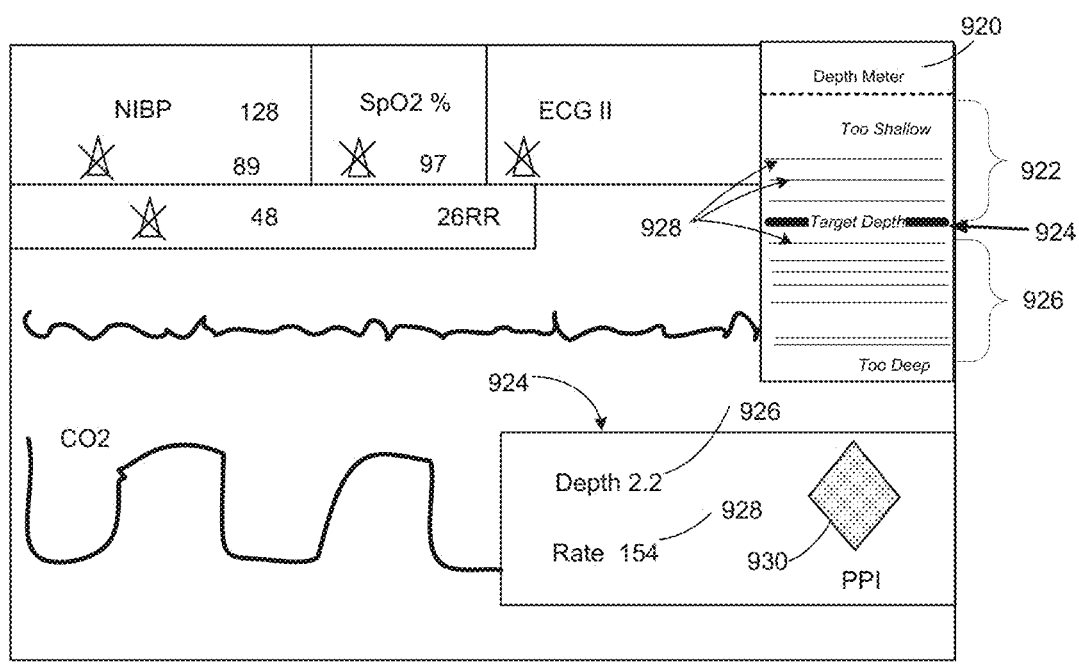
FIGS. 9A and 9B show screenshots with gradiated scales indicating target chest compression depths.

As shown in FIG. 9A, a visual representation of CPR quality can include an indicator of CPR compression depth such as a CPR depth meter 920. The CPR depth meter 920 can be automatically displayed upon detection of CPR chest compressions.

On the CPR depth meter 920, depth bars 928 visually indicate the depth of the administered CPR compressions relative to a target depth 924. As such, the relative location of the depth bars 928 in relation to the target depth 924 can serve as a guide to a rescuer for controlling the depth of CPR compressions. For example, depth bars 928 located in a region 922 above the target depth bar 924 indicate that the compressions were shallower than the target depth, and depth bars 928 located in a region 926 below the target depth bar 924 indicate that the compressions were deeper than the target depth. Again, then depth is inadequate (along with perhaps other factors) for a sufficient time to indicate that the rescuer is fatiguing, an indicator to switch rescuers can be provided in the manners discussed above.

Figure 9B:
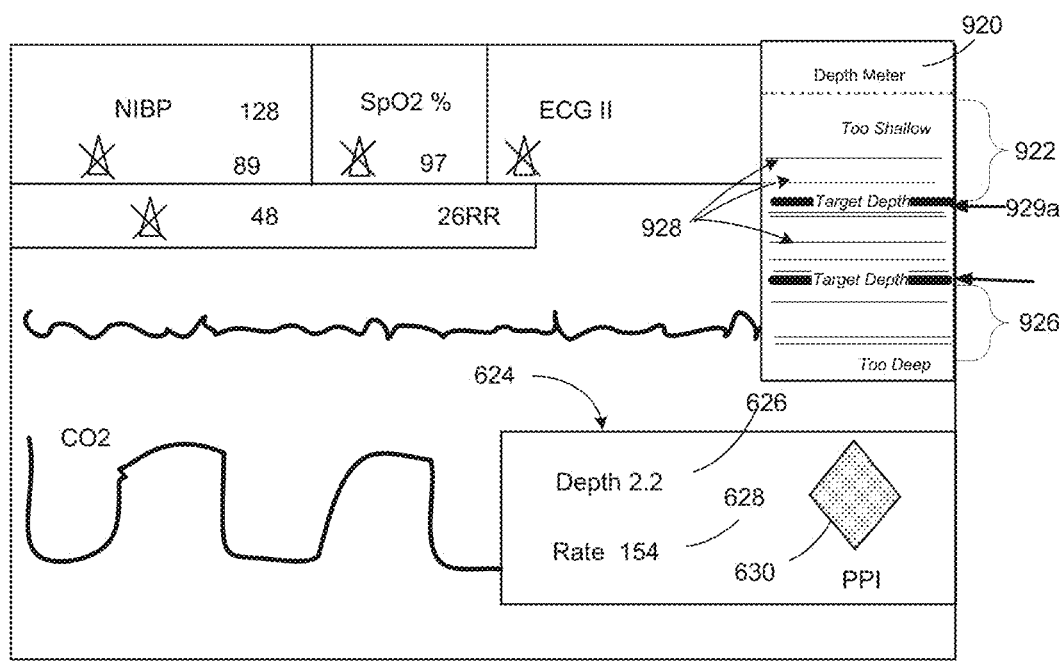

While the example shown in FIG. 9A displayed the target depth 924 as a single bar, in some additional examples, the target depth can be displayed as a range of preferred depths. For example, two bars 929a and 929b can be included on the depth meter 920 providing an acceptable range of compression depths (e.g., as shown in FIG. 9B). Additionally, in some implementations, compressions that have depths outside of an acceptable range can be highlighted in a different color than compressions that have depths within the acceptable range of compression depths.

The depth bars 928 displayed on the CPR depth meter 920 can represent the compression depths of the most recent CPR compressions administered by the rescuer. For example, the CPR depth meter 920 can display depth bars 928 for the most recent 10-20 CPR compressions (e.g., the most recent 10 CPR compressions, the most recent 15 compressions, the most recent 20 CPR compressions). In another example, CPR depth meter 920 can display depth bars 928 for CPR compressions administered during a particular time interval (e.g., the previous 10 seconds, the previous 20 seconds).

In some additional embodiments, physiological information (e.g., physiological information such as end-tidal CO2 information, arterial pressure information, volumetric CO2, pulse oximetry (presence of amplitude of waveform possibly), and carotid blood flow (measured by Doppler) of the patient (and in some cases, the rescuer) can be used to provide feedback on the effectiveness of the CPR delivered at a particular target depth. Based on the physiological information, the system can automatically determine a target CPR compression depth (e.g., calculate or look-up a new CPR compression target depth) and, for example, provide feedback to a rescuer to increase or decrease the depth/rate of the CPR compressions. Such feedback may involve guidance for the rescuer to adjust his/her kinematic position and/or body motion to achieve a desired combination of CPR compressions (e.g., depth, rate), rescuer fatigue and/or physiological outcome. Thus, the system can provide both feedback related to how consistently a rescuer is administering CPR compressions at a target depth/rate, and feedback related to whether the target depth/rate should be adjusted based on measured physiological parameters, along with how the rescuer may enhance his/her body positioning in administering CPR. If the rescuers do not respond to such feedback and continues performed sub-optimal CPR, the system can then display an additional message to switch out the person performing CPR chest compressions.

In some implementations, the system regularly monitors and adjusts the target CPR compression depth. In order to determine a desirable target depth, the system makes minor adjustments to the target CPR compression depth and observes how the change in compression depth affects the observed physiological parameters before determining whether to make further adjustments to the target compression depth. More particularly, the system can determine an adjustment in the target compression depth that is a fraction of an inch and prompt the rescuer to increase or decrease the compression depth by the determined amount. For example, the system can adjust the target compression depth by 0.1-0.25 inches (e.g., 0.1 inches to 0.15 inches, 0.15 to 0.25 inches, about 0.2 inches) and provide feedback to the rescuer about the observed compression depth based on the adjusted target compression depth. Then, over a set period of time, the system can observe the physiological parameters and, based on trends in the physiological parameters without making further adjustments to the target compression depth and at the end of the set time period, can determine whether to make further adjustments to the target compression depth.

And again, the actual performance of the rescuer against the revised target can be continually monitored to determine when the rescuer's performance has fallen below an acceptable level, so that the rescuer and perhaps others can be notified to change who is performing the chest compressions. Also, each of the relevant parameters of patient condition discussed above with respect to the various screenshots can be made one of multiple inputs to a process for determining when rescuers who are performing one component of a rescue technique should be switched out with another rescuer, such as for reasons of apparent fatigue on the part of the first rescuer.

While at least some of the embodiments described above describe techniques and displays used during manual human-delivered chest compressions, similar techniques and displays can be used with automated chest compression devices such as the AUTOPULSE device manufactured by ZOLL Medical, MA.

Figure 10A:
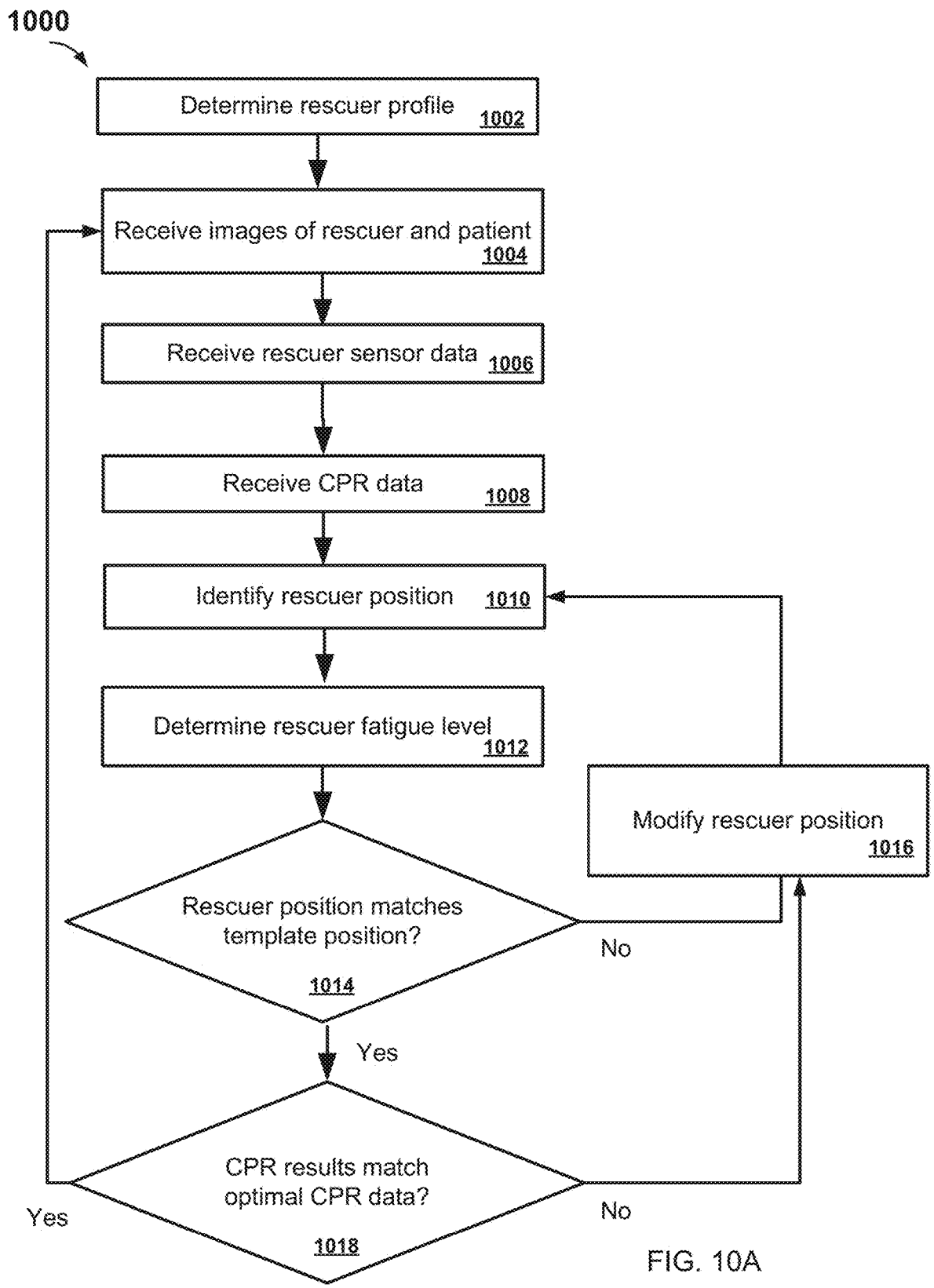
FIGS. 10A and 10B are flow charts of example processes for assisting a rescuer to perform CPR.

FIG. 10A is a flowchart of an example of a process 1000 for monitoring CPR performance and providing feedback for improvement of the performance. Generally, the process involves automatic monitoring of the performance of a component of CPR, such as the provision of chest compressions to a patient, and the indication to a rescuer who provides of such a treatment when and how to update a body position. The process can start at 1002, by retrieving a rescuer profile for one or all of the rescuers who are present at the rescue scene. An example process of retrieving the rescuer profile is described with reference to FIG. 10B.

At 1004, the process monitors, using a camera and one or more processors, a rescuer performing the CPR treatment, chest compressions that are performed on a patient. The images of the rescuer are being acquired by the camera positioned near to the rescuer, as described with reference to FIGS. 1A-1D. The images can be acquired as a video data recorded at a particular rate (e.g., 5-20 frames/s). In some implementations, images of the rescuer are recorded in parallel to additional visual data, such as images of the patient and distance data, forming an animated three dimensional representation of the rescue scene. Images of the rescuer are processed to identify a set of rescuer positions in real-time.

At 1006, rescuer sensor data is optionally received from one or more sensors that are attached to the rescuer and configured to sense one or more parameters representative of a fatigue level of the rescuer. The one or more sensors can be configured to monitor any one of heart rate, respiration rate, blood pressure, muscle pH, and lactate content. The signals acquired by the sensors attached to the rescuer (e.g., sensors described with reference to FIGS. 3A and 3B) can be processed by a processor integrated in the nearby defibrillator or at a central system located in a remote medical facility. At 1008, CPR patient data is optionally received from a set of patient sensors configured to sense one or more signals associated to the CPR treatment being provided. The patient sensors can be configured to measure ECG, ETCO2, SpO2, blood pressure and/or SmO2.

At 1008, the acquired images of the rescue scene are processed in real-time. In some implementations, the rescuer images are filtered to remove any interference that may arise from the background and maintain a 3D body contour of the rescuer. The body contour of the rescuer is processed to identify the location of particular rescuer body regions relative to other body regions and evaluate them based on a CPR protocol. In some implementations, the rescuer body regions are identified using a body region coordinate calculation based on 3D system of Cartesian coordinates. For example, each individual frame can be individually processed to determine the coordinates of each portion of the rescuer's body. Each identified portion of the rescuer's body, can correspond to a part of interest of the rescuer's body, such as the elbows and the shoulders. Each portion of the rescuer's body can be identified based on calculating the Cartesian coordinates of a center of each portion of the rescuer's body. In some implementations, each portion of the rescuer's body is identified based on one or more markers that are attached to the corresponding region the of the rescuer's body. Such portions may include any one of the shoulders, elbows, wrists, hips, and/or other parts of the body relevant for providing quality CPR. For example, the portions of interest of the rescuer's body can be automatically identified by using feature and pattern recognition algorithms or they can be initially identified in the first acquired image by a user interacting with the display. The portions of interest of the rescuer's body can be automatically tracked in subsequent images in real-time during CPR treatment by using displacement tracking algorithms (e.g., by correlating subsequently acquired images).

The processed images, including the identification of the regions of interest can form a 3D rescuer body model including characteristics of a rescuer motion over one or more periods of time. In some implementations, the results of several images are being averaged to improve the accuracy of the 3D rescuer body model. The 3D rescuer body model can be displayed (e.g., by the display of the defibrillator or a mobile device that can be operated by the rescuer performing CPR) in 2D or 3D, as mimicking the positions of the rescuer in real-time. In some implementations, the generation of the 3D rescuer body model can include a body size data calculation unit for generating additional physical data of the rescuer. The physical data of the rescuer can be used to generate a 3D shape of a template body. A set of multiple optimal positions of the template body can be generated based on the adopted CPR protocol, as described with reference to FIGS. 2A-2D. The positions of the template body can be displayed as being superimposed over the rescuer body model. A shape model and a template mode that match the size of the rescuer enhance the ability of the rescuer to understand the display and to correct the body position during CPR. The generation of 3D shape model and 3D template body enable the differentiation between the rescuer position and the template position.

At 1012, a rescuer fatigue level is optionally determined by using acquired fatigue related data. In some implementations, the rescuer fatigue level can be determined at preset intervals (e.g., at a particular CPR phase or at a predetermined interval, independent of the CPR cycle). In some implementations, the rescuer fatigue level can be automatically analyzed as a trend relative to the duration of the CPR treatment performed by the rescuer.

At 1014, each rescuer position is associated with a CPR phase (e.g., by using the accelerometer puck), such as compression downstroke/upstroke and, for the particular phase of CPR, is compared to a corresponding template position. The rescuer's position and the template position can be compared using the 3D Cartesian system of coordinates. If the rescuer's position is determined to not be adequately similar to the recommended template position, at 1016, the process provides an indication to the rescuer, and perhaps to others, that the rescuer's position should change. For example, the real-time feedback is provided to instruct the rescuer to straighten elbows during a chest compression phase of CPR, to maintain shoulders above the sternum of the patient and hands of the rescuer, and/or to fully release during a chest decompression phase of CPR.

In some implementations, the feedback is provided on the display, through the rescuer's attached electrodes and through audio instructions. For example, visual indications can be given on a display of a defibrillator or can be displayed on a device mounted close to the location where the rescuer is performing the particular component of CPR, such as adjacent to the hands of the rescuer when the hands are pressing on the sternum of a patient. In addition, haptic feedback can be provided to the rescuer, such as switching from periodic (metronomic) vibration in a particular location of the rescuer's CPR assistance garment, or a puck placed under the rescuer's hands, or another change in haptic feedback that differs from the feedback given when the rescuer's position is correct. The modification of the rescuer's position is monitored and the process returns to 1010 to identify whether the updated position of the rescuer is correct.

If the CPR quality and/or manner in which the CPR is administered (e.g., via kinematic analysis) is determined to be acceptable, the process continues to 1018 and CPR results are compared to expected CPR data. For example, patient data is being analyzed and if the patient does not react to the provided CPR treatment a variation in CPR treatment might be recommended. In some implementations, the variation in CPR treatment requires a change in rescuer' position and process returns back to 1016 and continues monitoring the chest compressions using the accelerometer puck and determining the quality of such compressions.

Using such a process, a rescuer can adjust the position in real-time to provide CPR compressions in an optimal way as long as they are able to provide for it. As a result, the system need not be stuck to preset time limits that might not reflect the actual standard of care that can be provided, but can instead vary based on the actual standard of care that is being given by a particular rescuer team in a particular situation. The process could result in better outcomes for patients tended to by such rescuers, and in a better experience for the rescuers themselves.

In some circumstances, prompts for performing CPR can change the way in which CPR is to be performed in response to indications that there has been a degradation in performance. In particular, prompting of CPR at a sub-optimal level can be provided, as long as that sub-optimal level is better than wholly fatiguing a rescuer. For example, hemodynamics data indicates that depth of chest compressions can be more important to patient well-being than is rate of compressions (e.g., it essentially does not matter how fast you are performing compressions if none of those compressions is truly effective). As a result, the system can guide the rescuer to perform chest compressions at a slower rate (e.g., a metronome) and can monitor how the depth of compressions changes in response to the prompted change in rate. Using stored hemodynamic data correlating depths and rates to effectiveness, the system can identify a most-preferred rate that maximizes the hemodynamic effect for a particular rescuer (using, e.g., the well-known Windkessel model or other approach). While such modifications can be made only after sensing that a particular rescuer is fatiguing, they can also be initiated at other points and in response to other criteria, including by making such adjustments throughout a rescue cycle (e.g., the rate of a metronome can be adjusted slightly and essentially continuously, and the combination of depth and rate that is measured from the rescuer can be input in real-time to a formula for computing hemodynamic effect, with subsequent changes in the rate of the metronome being made in an attempt to increase the hemodynamic effect within bounds of safety).

Figure 10B:
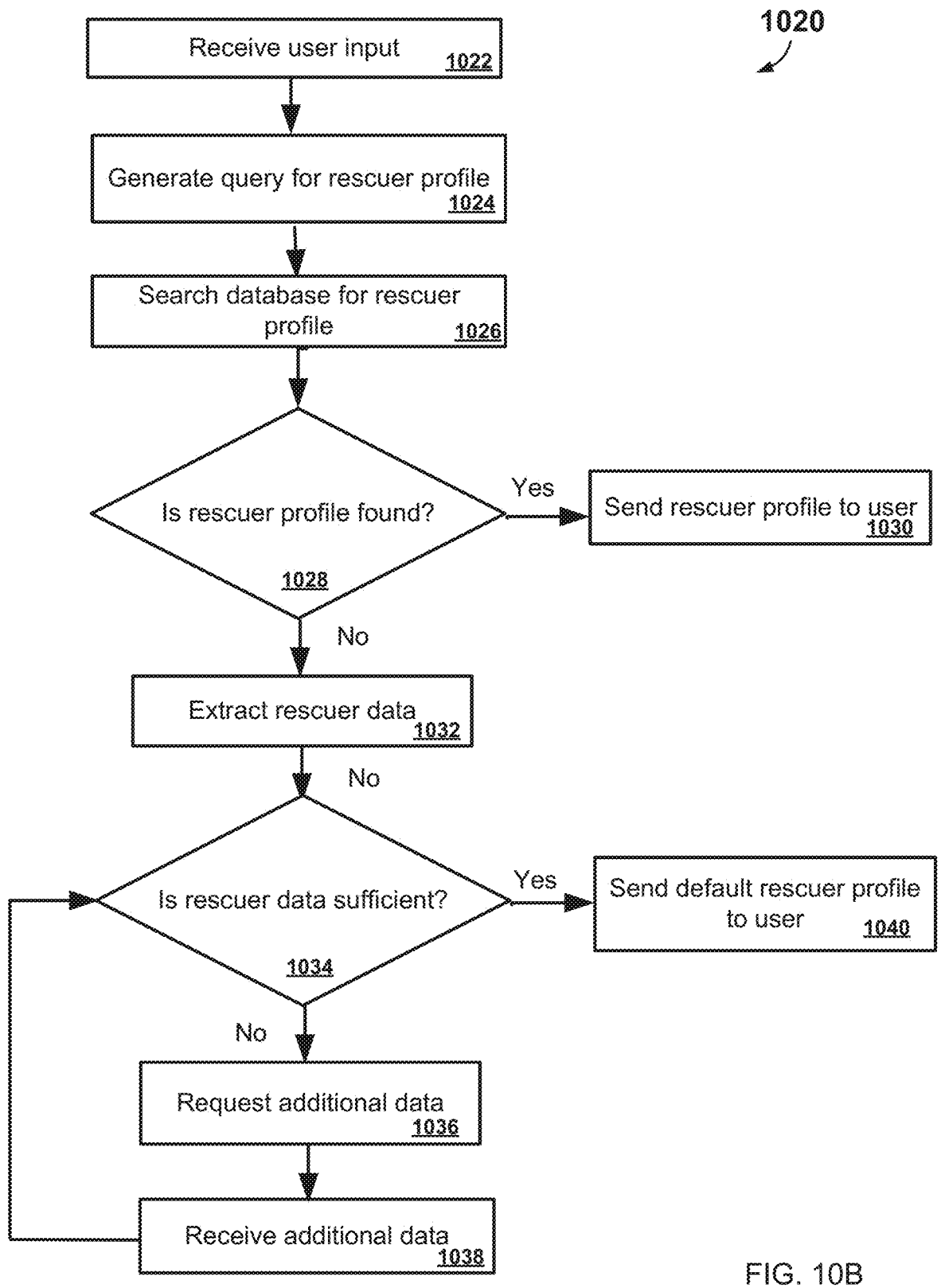

FIG. 10B is a flowchart of an example of a process 1020 for retrieving a rescuer profile that could be used during a process of assisting CPR treatment, as described with reference to FIG. 10A.

The process can start at 1022, by receiving a user input. For example, the processor 120 of FIGS. 1A-1D can receive a user request from the defibrillator 112 or a mobile device 110. In some implementations, the user input is received from a rescuer (e.g., any of rescuers 104 or 106 in FIGS. 1A-1D), who is present at or is travelling towards a rescue scene. The user input can also be received from a remote user (e.g., rescuer 108 in FIGS. 1A-1D) who has access to information related to a rescuer who is scheduled to perform a CPR treatment. The user input can also be generated automatically by the system 100 described with reference to FIGS. 1A-1D in response to a determination that CPR treatment is being performed on a patient. The user input can include a request for a rescuer profile.

In some examples, the request includes a user identifier, a rescuer identifier, a device identifier, a patient identifier, rescuer data identifiers, patient information identifiers and additional rescuer data. In some examples, the user identifier can be used to determine the particular user, who can be different from the rescuer and has issued the request. The device identifier can be used to determine the particular device that transmitted the request. The rescuer identifier can identify the rescuer who is scheduled to perform or is currently performing a CPR treatment. The rescuer identifier can be determined based on receiving an input from a user interface. The rescuer identifier can be derived from a rescuer identity. The identity of the rescuer can be determined based on analyzing one or more rescuer images. The patient identifier identifies the particular patient that is the subject to the CPR treatment. The rescuer data identifiers identify the rescuer specific profile that has been requested (e.g., 3D images of optimal rescuer positions for CPR) and the additional data identifiers identify additional data that has been requested.

Additional rescuer data can include rescuer fitness indicators, indications of the quality of the chest compression, and number of rescuers at the rescue scene. For example, as a rescuer sets up a defibrillator and connects it to a patient, the defibrillator can ask the rescuer (on a display or via a spoken request) for particular rescuer data (e.g., data related to general and current fitness level of the rescuer) that can be used to retrieve a rescuer profile. General fitness related indicators can include gender, age, weight, height, exercise type, exercise frequency, and CPR experience. Current fitness related indicators can include estimate of current energy level and/or stress level. Some fitness related indicators can be provided by the rescuer and some fitness related indicators can be automatically inferred. For example, a 3D image of the rescuer can be analyzed to identify a body type (e.g., weight and height). The rescuer's fitness level can be used to determine an ability of the rescuer to perform the CPR treatment.

The indications of the quality of the chest compression and/or the motion/position of the rescuer during chest compressions can also be automatically retrieved through processing signals acquired at the rescue scene. For example, the process 1020 can be executed after the rescuer began performing chest compressions on the patient. Such compressions can cause a puck to move and accelerate up and down, so that an accelerometer in the puck generates signals indicative of such acceleration. The defibrillator can receive such signals and convert them into indications of the quality of the chest compression, such as indications of how deep each test compression is, and the pace at which particular ones of the chest compressions are occurring. Before the monitoring begins, the process can have rescuer data gathered to aid in the optimization of the CPR performance.

In some implementations, the defibrillator can ask the rescuer whether the rescuer is alone or is being aided, and might also ask how many additional rescuers are available. If the rescuer indicates that he or she is alone, then the system can follow a branch of programming that does not recommend switching of rescuers, but might provide a particular feedback that prevents immediate fatigue of the rescuer. If the rescuer is accompanied, then the system can subsequently indicate when rescuers are to switch roles. The system can also assign a label to each rescuer, such as "Rescuer 1" and "Rescuer 2" or the actual names of the rescuers (which could have been programmed previously, such as for EMTs who use the system frequently, or could be obtained, such as by lay rescuers speaking their names into the device in response to prompts from the device). If there are three or more rescuers, instructions for rotating can be more complex—e.g., involving more than simply an instruction to switch positions, but instead telling each rescuer what component of CPR they should be performing for any particular time period.

A determination about the number of rescuers can also be made inferentially. For example, a ventilation bag can include electronics that report to a defibrillator or other box, and can further sense that the bag is being deployed or used, or is being used simultaneously with chest compressions being performed, in order to infer that there are at least two rescuers. The defibrillator can adjust its operation accordingly in the manners discussed above in such a situation (e.g. by enabling prompts for rescuers to switch roles).

In the example data flow 1020, the processor receives the request and processes the request to validate the request and to authenticate the user, who submitted the request (e.g., based on the user identifier and/or the device identifier). At 1024, upon validation and/or authentication, the processor generates a query for the rescuer profile and provides the query to a database (e.g., database 120 in FIGS. 1A-1D). At 1026, the database is searched for a rescuer specific profile. In some examples, it can be determined that the rescuer specific profile required to fulfill the request can be provided from a data cache module (e.g., reposed mode). In such examples, the patient data/information is provided to the processor (e.g., processor of defibrillator 112 of FIGS. 1A-1D) from the data cache module. In some examples, it can be determined that that the rescuer specific profile required to fulfill the request is to be retrieved from one or more data sources across a healthcare continuum of the rescuer (e.g., federated mode).

In some examples, if the rescuer specific profile required to fulfill the request is to be retrieved from one or more data sources across the healthcare continuum (e.g. federated mode), request information is transmitted over a network to one or more databases. In some examples, the processor can be aware of which database of which facility system can be searched to retrieve the rescuer specific profile from (e.g., based on the rescuer-to-database/facility index).

At 1028, the processor identifies if the rescuer specific profile is found. A rescuer specific profile can include a time interval to fatigue, a history of training, and a set of template positions. The set of template positions retrieved based on the rescuer identifier can include images (e.g., 3D images/animations) acquired during previously successful CPR treatments or training sessions performed by the identified rescuer. The set of template positions can be CPR positions associated with maximum CPR success based on a rescuer skill level, such as beginner, novice, intermediate and expert. In some implementations, the processor can also verify a validity of the found rescuer specific profile. For example, the processor can be configured to perform a validation process, such that an old rescuer specific profile is checked to identify its usefulness value. The validation process can include an updating process based on additional rescuer data. For example, a rescuer profile indicating a particular level (e.g., an expert level) for a rescuer who has not performed a CPR for more than a predetermined period of time (e.g., past 5 years) can be downgraded to a lower level (e.g., an intermediate level).

At 1030, if the rescuer specific profile is found, the rescuer specific profile is sent to the user or may otherwise be loaded into the system for evaluating the body position/motion of the rescuer according to an appropriate template while administering chest compressions. At 1032, if a rescuer specific profile is not found the rescuer data is extracted for retrieving a matching default rescuer profile. In some implementations, the additional rescuer data is extracted by processing the user input. At 1034, the additional rescuer data is evaluated to determine whether rescuer data is sufficient to retrieve a matching default rescuer profile. At 1036, if the previously provided rescuer data is not sufficient (e.g., rescuer fitness data is missing), additional data is requested. At 1038, once the additional data is received, the process returns to 1034 to reevaluate whether the rescuer data is sufficient to generate or to retrieve a matching default rescuer profile.

At 1040, if the rescuer data is sufficient, the default rescuer profile can be retrieved from a database so that the kinematic behavior of the rescuer during chest compressions can be evaluated. For example, the default rescuer profile can be selected based on general and current fitness related indicators. Based on the ability of the rescuer to perform the CPR treatment, a preexistent CPR rescuing model including a set of template positions is selected. The retrieved set of template positions can include matching body models derived from images acquired during previously successful CPR treatments or training sessions performed by other rescuers or they can be based on computer models of optimal CPR treatments.

Figure 11:
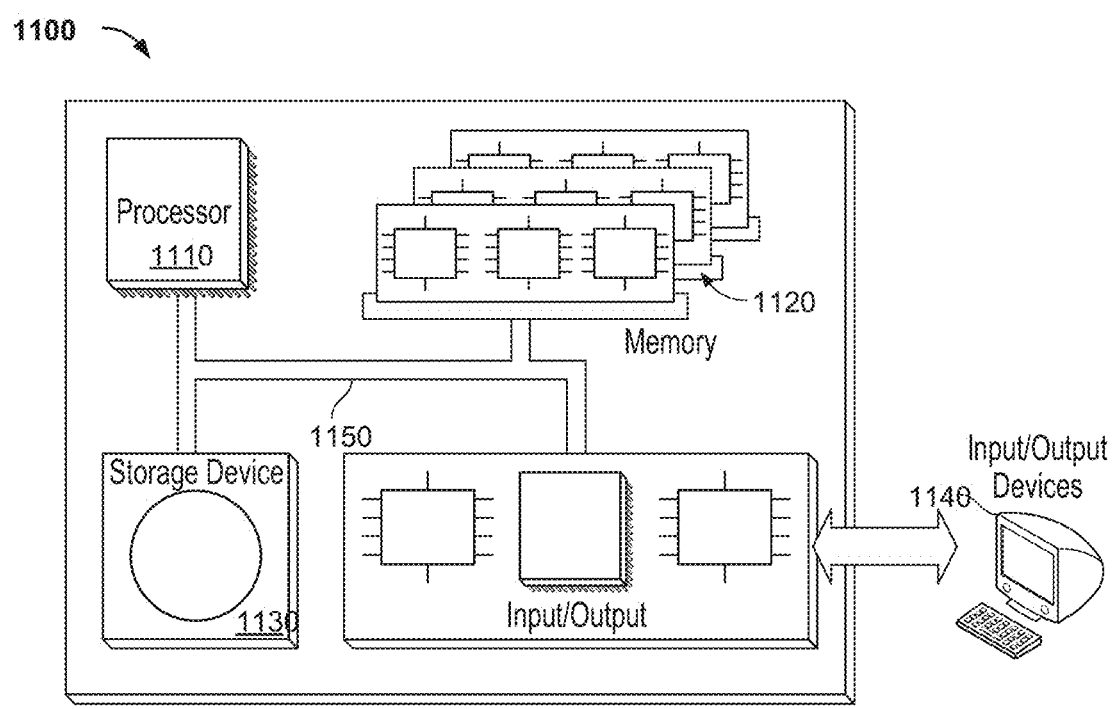
FIG. 11 shows a general computer system that can provide interactivity with a user of a medical device, such as feedback to a user in the performance of CPR.

The described techniques can be assisted by the use of a computer-implemented medical device, such as a defibrillator that includes computing capability. Such defibrillator or other device is shown in FIG. 11, and can communicate with and/or incorporate a computer system 1100 in performing the operations discussed above, including operations for computing the quality of one or more components of CPR provided to a patient and generating feedback to rescuers, including feedback to change rescuers who are performing some components of the CPR. The system 1150 can be implemented in various forms of digital computers, including computerized defibrillators laptops, personal digital assistants, tablets, and other appropriate computers. Additionally, the system can include portable storage media, such as, Universal Serial Bus (USB) flash drives. For example, the USB flash drives can store operating systems and other applications. The USB flash drives can include input/output components, such as a wireless transmitter or USB connector that can be inserted into a USB port of another computing device.

The system 1150 includes a processor 1110, a memory 1120, a storage device 1130, and an input/output device 1140. Each of the components 1110, 1120, 1130, and 1140 are interconnected using a system bus 1150. The processor 1110 is capable of processing instructions for execution within the system 1150. The processor can be designed using any of a number of architectures. For example, the processor 1110 can be a CISC (Complex Instruction Set Computers) processor, a RISC (Reduced Instruction Set Computer) processor, or a MISC (Minimal Instruction Set Computer) processor.

In one implementation, the processor 1110 is a single-threaded processor. In another implementation, the processor 1110 is a multi-threaded processor. The processor 1110 is capable of processing instructions stored in the memory 1120 or on the storage device 1130 to display graphical information for a user interface on the input/output device 1140.

The memory 1120 stores information within the system 1150. In one implementation, the memory 1120 is a computer-readable medium. In one implementation, the memory 1120 is a volatile memory unit. In another implementation, the memory 1120 is a non-volatile memory unit.

The storage device 1130 is capable of providing mass storage for the system 1150. In one implementation, the storage device 1130 is a computer-readable medium. In various different implementations, the storage device 1130 can be a floppy disk device, a hard disk device, an optical disk device, or a tape device.

The input/output device 1140 provides input/output operations for the system 1150. In one implementation, the input/output device 1140 includes a keyboard and/or pointing device. In another implementation, the input/output device 1140 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform some activity or bring about some result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having an LCD (liquid crystal display) or LED display for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

Many other implementations other than those described can be employed, and can be encompassed by the following claims.

What is claimed is:

1. A system for managing a cardiopulmonary resuscitation (CPR) treatment to a patient in need of emergency assistance by a rescuer, the system comprising:
  a camera configured to capture images of a rescuer performing the CPR treatment onsite on the patient at a rescue scene; and
  one or more processors, in communication with the camera, configured to:
    receive the images of the rescuer, the images of the rescuer comprising a plurality of markers associated with a plurality of portions of rescuer's body,
    analyze the plurality of markers to determine body position data of the rescuer onsite at the rescue scene by using at least one feature and pattern recognition algorithm based on an image correlation method to automatically track displacement of positions of the plurality of markers by determining displacement variations among subsequently acquired images of the rescuer onsite at the rescue scene, the subsequently acquired images comprising the plurality of markers,
    select based on a request, a rescuer profile for the rescuer at the rescue scene, the rescuer profile comprising characteristics of the rescuer defining a body type,
    generate a body position comparison by comparing the body position data to data representing one or more positions of a template body generated based on the rescuer profile,
    generate an indication of the body position comparison of the body position data to the data representing the one or more positions of the template body, and
    cause real-time feedback to be provided to the rescuer to adjust a manner in which the CPR treatment is provided based on the body position comparison, wherein the real-time feedback comprises providing by a CPR treatment assisting device at least one of: a haptic signal, a visual display, and a virtual reality support.

2. The system of claim 1, wherein the images of the rescuer comprise data relevant to an ability of the rescuer to perform the CPR treatment.

3. The system of claim 2, wherein the rescuer profile comprises data identifying a skill level of the rescuer, wherein the rescuer profile is at least one of an expert profile, an intermediate profile, a novice profile, a default profile, and a profile that is optimized for the rescuer based off of previous testing or mock rescue attempts.

4. The system of claim 2, wherein the data representing physical characteristics of the rescuer comprises data representing a history of training.

5. The system of claim 1, wherein the body position of the rescuer is at least one of a static body position and a dynamic body position.

6. The system of claim 1, wherein the real-time feedback is provided to the rescuer in a sequence of instructions based on a phase of the CPR treatment.

7. The system of claim 1, wherein the one or more processors are configured to analyze the images by generating a three dimensional representation of the rescue scene, the three dimensional representation comprising a first representation of at least a portion of the rescuer and a second representation of at least a portion of the patient in need of emergency assistance by the rescuer.

8. The system of claim 7, wherein generating the three dimensional representation of the rescue scene comprises removing information sufficient to identify the patient from the three dimensional representation.

9. The system of claim 1, wherein the one or more processors are configured to determine an identity of the rescuer and select a profile associated with the rescuer based on the identity.

10. The system of claim 9, wherein the identity of the rescuer is determined based on at least one of analyzing the images and receiving an input from a user interface.

11. The system of claim 1, wherein the real-time feedback comprises an audio signal.

12. The system of claim 11, wherein the visual display comprises guidance to the rescuer for administering the CPR treatment.

13. The system of claim 12, wherein the guidance to the rescuer comprises one or more images providing instruction of how to modify the body position of the rescuer.

14. The system of claim 11, wherein the haptic signal is communicated to a haptic garment worn by the rescuer, the haptic garment comprising one or more feedback devices configured to deliver haptic feedback to the rescuer wearing the garment, and the one or more feedback devices are configured to deliver haptic feedback to at least one of the arms, elbows, shoulders, hips and torso of the rescuer.

15. The system of claim 1, wherein the real-time feedback to the rescuer indicates a modified position of the rescuer, the modified position representing a template position for the CPR treatment.

16. The system of claim 15, wherein the one or more processors are in communication with the one or more sensors, and the one or more processors are configured to analyze the one or more parameters to determine a fatigue level of the rescuer.

17. The system of claim 16, comprising:
an electronic patient monitor;
a set of patient sensors configured to sense one or more signals associated to the CPR treatment being provided; and
a CPR monitor included in an electronic patient monitor and configured to use an input from the set of patient sensors to identify and display a quality level of the CPR treatment being provided.

18. The system of claim 17, wherein the electronic patient monitor is a mobile device.

19. The system of claim 17, wherein the quality level of the CPR treatment is used to determine the real-time feedback to the rescuer.

20. The system of claim 19, wherein the quality level of the CPR treatment reflects a depth of chest compressions, rate of compression, or both.

21. The system of claim 17, wherein the electronic patient monitor is part of an external patient defibrillator.

22. The system of claim 16, wherein the one or more processors are configured to transmit the fatigue level of the rescuer to a central management system.

23. The system of claim 16, wherein the one or more processors are configured to transmit the fatigue level of the rescuer to one or more devices associated with other rescuers that are attending to the patient.

24. The system of claim 1, wherein the real-time feedback is provided to instruct the rescuer to perform at least one of the following actions: straighten elbows during a chest compression phase of CPR, maintain shoulders above the sternum of the patient and hands of the rescuer, and fully release during a chest decompression phase of CPR.

25. The system of claim 1, wherein analyzing the images to determine the body position of the rescuer comprises processing data associated with visual markers attached to the rescuer.

26. The system of claim 1, wherein the one or more processors are configured to:
provide the comparison of the body position data to the data representing the one or more positions of the template body to a defibrillator for display.

27. The system of claim 26, wherein the defibrillator is configured to provide an indicator of when the rescuer should change with a second rescuer, based at least in part, on an identified rescuer profile.

28. The system of claim 27, wherein the one or more processors, in communication with the camera, is configured to:
determine that the rescuer changed with the second rescuer; and
identify a second rescuer profile in response the rescuer changing with the second rescuer.

29. The system of claim 1, wherein the rescuer profile comprises one or more of: fitness related indicators, body postures, amplitudes of compression, success in CPR treatment, duration to fatigue, and ability to respond to audio and video signals from an area around a test subject during CPR treatment.

30. The system of claim 1, wherein the one or more processors, in communication with the camera, is configured to analyze the images to determine a fatigue level of the rescuer.

* * * * *

UNITED STATES PATENT AND TRADEMARK OFFICE
CERTIFICATE OF CORRECTION

PATENT NO. : 11,219,575 B2  
APPLICATION NO. : 15/463678  
DATED : January 11, 2022  
INVENTOR(S) : Christopher Luke Kaufman, Ulrich Herken and Gary A. Freeman Page 1 of 1

It is certified that error appears in the above-identified patent and that said Letters Patent is hereby corrected as shown below:

On the Title Page

Column 2, item (56), Line 1, under "OTHER PUBLICATIONS", delete "Futhre," and insert -- Future, --

Column 2, item (57), Line 3, delete "cardio-pulmonary" and insert -- cardiopulmonary --

Signed and Sealed this  
Fifth Day of April, 2022

Drew Hirshfeld  
*Performing the Functions and Duties of the  
Under Secretary of Commerce for Intellectual Property and  
Director of the United States Patent and Trademark Office*